(12) United States Patent
Seex

(10) Patent No.: US 10,687,860 B2
(45) Date of Patent: Jun. 23, 2020

(54) SEGMENTAL CORRECTION OF LUMBAR LORDOSIS

(71) Applicant: Retrospine Pty Ltd, Sydney, NSW (AU)

(72) Inventor: Kevin Seex, Sydney (AU)

(73) Assignee: RETROSPINE PTY LTD, Sydney (AU)

( * ) Notice: Subject to any disclaimer, the term of this patent is extended or adjusted under 35 U.S.C. 154(b) by 0 days.

(21) Appl. No.: 14/150,671

(22) Filed: Jan. 8, 2014

(65) Prior Publication Data

US 2014/0249584 A1  Sep. 4, 2014

Related U.S. Application Data

(63) Continuation-in-part of application No. 14/045,709, filed on Oct. 3, 2013, now abandoned, which is a continuation of application No. 13/869,855, filed on Apr. 24, 2013, now abandoned.

(60) Provisional application No. 61/637,650, filed on Apr. 24, 2012, provisional application No. 61/884,803, filed on Sep. 30, 2013.

(51) Int. Cl.
   *A61B 17/70* (2006.01)

(52) U.S. Cl.
   CPC .................. *A61B 17/7043* (2013.01)

(58) Field of Classification Search
   CPC .............. A61B 17/7043; A61B 17/705; A61B 17/7049; A61B 17/7052; A61B 17/7014; A61B 17/7019; A61B 17/7023; A61B 17/7025; A61B 17/8023
   USPC .................................... 606/71, 259
   See application file for complete search history.

(56) References Cited

U.S. PATENT DOCUMENTS

| | | | | |
|---|---|---|---|---|
| 5,180,393 | A | * | 1/1993 | Commarmond .... A61B 17/7007 606/254 |
| 5,387,212 | A | * | 2/1995 | Yuan .................... A61B 17/701 606/264 |
| 5,437,669 | A | * | 8/1995 | Yuan .................. A61B 17/7047 606/264 |
| 5,470,333 | A | * | 11/1995 | Ray .................... A61B 17/7055 606/261 |
| 5,531,745 | A | * | 7/1996 | Ray .................... A61B 17/7055 606/261 |
| 5,667,506 | A | | 9/1997 | Sutterlin |
| 5,688,275 | A | * | 11/1997 | Koros ................ A61B 17/7041 606/264 |

(Continued)

FOREIGN PATENT DOCUMENTS

WO   WO-2010090428 A2 *  8/2010 ......... A61B 17/7023

OTHER PUBLICATIONS

Santoni et al., "Cortical bone trajectory for lumbar pedicle screws," The Spine Journal, May 2009, pp. 366-373, vol. 9, No. 5.

*Primary Examiner* — Jan Christopher L Merene
(74) *Attorney, Agent, or Firm* — Morriss O'Bryant Compagni Cannon, PLLC.

(57) ABSTRACT

A stabilizing apparatus for a spine comprising, a plurality of transverse rods, each of the transverse rods attached to a respective vertebra and a single link having an elongated through-hole, the single link enjoining a plurality of the transverse rods, wherein the single link enables longitudinal translation between enjoined transverse rods and substantially prevents lateral translation between enjoined transverse rods.

32 Claims, 22 Drawing Sheets

(56) References Cited

U.S. PATENT DOCUMENTS

| | | | |
|---|---|---|---|
| 5,702,392 A * | 12/1997 | Wu | A61B 17/7008 606/250 |
| 5,707,372 A | 1/1998 | Errico et al. | |
| 5,904,682 A * | 5/1999 | Rogozinski | A61B 17/7007 606/286 |
| 6,238,396 B1 * | 5/2001 | Lombardo | A61B 17/7052 606/251 |
| 6,432,108 B1 * | 8/2002 | Burgess | A61B 17/7052 606/252 |
| 6,458,131 B1 * | 10/2002 | Ray | A61B 17/7044 606/261 |
| 6,669,697 B1 * | 12/2003 | Pisharodi | A61B 17/7007 606/250 |
| 6,673,073 B1 | 1/2004 | Schafer | |
| 6,761,721 B2 | 7/2004 | Burgess et al. | |
| 6,916,319 B2 * | 7/2005 | Munting | A61B 17/7043 606/250 |
| 7,001,388 B2 | 2/2006 | Orbay et al. | |
| 7,041,105 B2 * | 5/2006 | Michelson | A61B 17/7059 606/247 |
| 7,220,262 B1 * | 5/2007 | Hynes | A61B 17/7011 606/279 |
| 7,250,052 B2 | 7/2007 | Landry et al. | |
| 7,306,603 B2 | 12/2007 | Boehm, Jr. et al. | |
| 7,438,715 B2 * | 10/2008 | Doubler | A61B 17/8042 606/280 |
| 7,473,269 B1 | 1/2009 | Hynes | |
| 7,485,132 B1 * | 2/2009 | McBride | A61B 17/7052 606/250 |
| 7,572,282 B2 | 8/2009 | Boomer et al. | |
| 7,691,145 B2 * | 4/2010 | Reiley | A61B 17/1671 606/247 |
| 7,766,940 B2 * | 8/2010 | Kwak | A61B 17/7043 606/246 |
| 7,967,845 B2 | 6/2011 | Lauryssen et al. | |
| 8,002,800 B2 * | 8/2011 | Winslow | A61B 17/7035 606/246 |
| 8,007,523 B2 | 8/2011 | Wagner et al. | |
| 8,043,345 B2 | 10/2011 | Carl et al. | |
| 8,048,121 B2 | 11/2011 | Mitchell et al. | |
| 8,048,123 B2 * | 11/2011 | Mitchell | A61B 17/7005 606/246 |
| 8,070,774 B2 | 12/2011 | Winslow et al. | |
| 8,097,024 B2 | 1/2012 | Winslow et al. | |
| 8,105,361 B2 | 1/2012 | Anderson et al. | |
| 8,162,988 B2 * | 4/2012 | Delecrin | A61B 17/7007 606/266 |
| 8,177,811 B2 * | 5/2012 | Tornier | A61B 17/7043 606/246 |
| 8,177,814 B2 * | 5/2012 | Predick | A61B 17/7044 606/250 |
| 8,357,182 B2 * | 1/2013 | Seme | A61B 17/7001 606/257 |
| 8,425,563 B2 * | 4/2013 | Firkins | A61B 17/705 606/259 |
| 8,496,686 B2 * | 7/2013 | Berg | A61B 17/7064 606/247 |
| 8,568,453 B2 * | 10/2013 | Abdou | A61B 17/7068 606/248 |
| 8,771,319 B2 * | 7/2014 | Prajapati | A61B 17/7052 606/250 |
| 8,828,056 B2 * | 9/2014 | Buss | A61B 17/7049 606/250 |
| 8,828,058 B2 * | 9/2014 | Elsebaie | A61B 17/7001 606/258 |
| 8,920,472 B2 * | 12/2014 | Seme | A61B 17/70 606/250 |
| 9,468,468 B2 * | 10/2016 | Seme | A61B 17/70 |
| 9,468,471 B2 * | 10/2016 | Otte | A61B 17/7052 |
| 2002/0188296 A1 * | 12/2002 | Michelson | A61B 17/7059 606/71 |
| 2005/0149030 A1 | 7/2005 | Serhan et al. | |
| 2006/0064092 A1 | 3/2006 | Howland | |
| 2006/0111714 A1 | 5/2006 | Foley | |
| 2006/0212033 A1 * | 9/2006 | Rothman | A61B 17/7028 606/328 |
| 2006/0265074 A1 * | 11/2006 | Krishna | A61B 17/7011 623/17.15 |
| 2006/0282080 A1 * | 12/2006 | Albert | A61B 17/7011 606/247 |
| 2007/0162000 A1 * | 7/2007 | Perkins | A61B 17/7062 606/249 |
| 2008/0281361 A1 * | 11/2008 | Vittur | A61B 17/7052 606/249 |
| 2008/0306529 A1 * | 12/2008 | Winslow | A61B 17/7005 606/246 |
| 2009/0036925 A1 * | 2/2009 | Sala | A61B 17/7023 606/246 |
| 2009/0043339 A1 * | 2/2009 | Tepper | A61B 17/7052 606/278 |
| 2009/0216277 A1 * | 8/2009 | Tornier | A61B 17/7011 606/250 |
| 2009/0228046 A1 * | 9/2009 | Garamszegi | A61B 17/7052 606/278 |
| 2009/0240280 A1 * | 9/2009 | Wang | A61B 17/7056 606/207 |
| 2009/0270861 A1 * | 10/2009 | Flandry, Jr. | A61B 17/7059 606/71 |
| 2010/0217322 A1 | 8/2010 | Predick | |
| 2010/0241167 A1 * | 9/2010 | Taber | A61B 17/7068 606/249 |
| 2011/0029020 A1 | 2/2011 | Gordon et al. | |
| 2011/0313323 A1 * | 12/2011 | Henderson | A61B 17/7055 600/594 |
| 2012/0083853 A1 * | 4/2012 | Boachie-Adjei | A61B 17/7038 606/86 A |
| 2012/0095512 A1 | 4/2012 | Nihalani | |
| 2012/0130436 A1 | 5/2012 | Haskins et al. | |
| 2013/0030468 A1 | 1/2013 | Le Couedic et al. | |
| 2013/0053888 A1 | 2/2013 | Torres | |
| 2013/0184762 A1 * | 7/2013 | Harper | A61B 17/7043 606/279 |
| 2013/0274803 A1 * | 10/2013 | Noordeen | A61B 17/7013 606/256 |
| 2013/0274807 A1 * | 10/2013 | Prajapati | A61B 17/7049 606/278 |

* cited by examiner

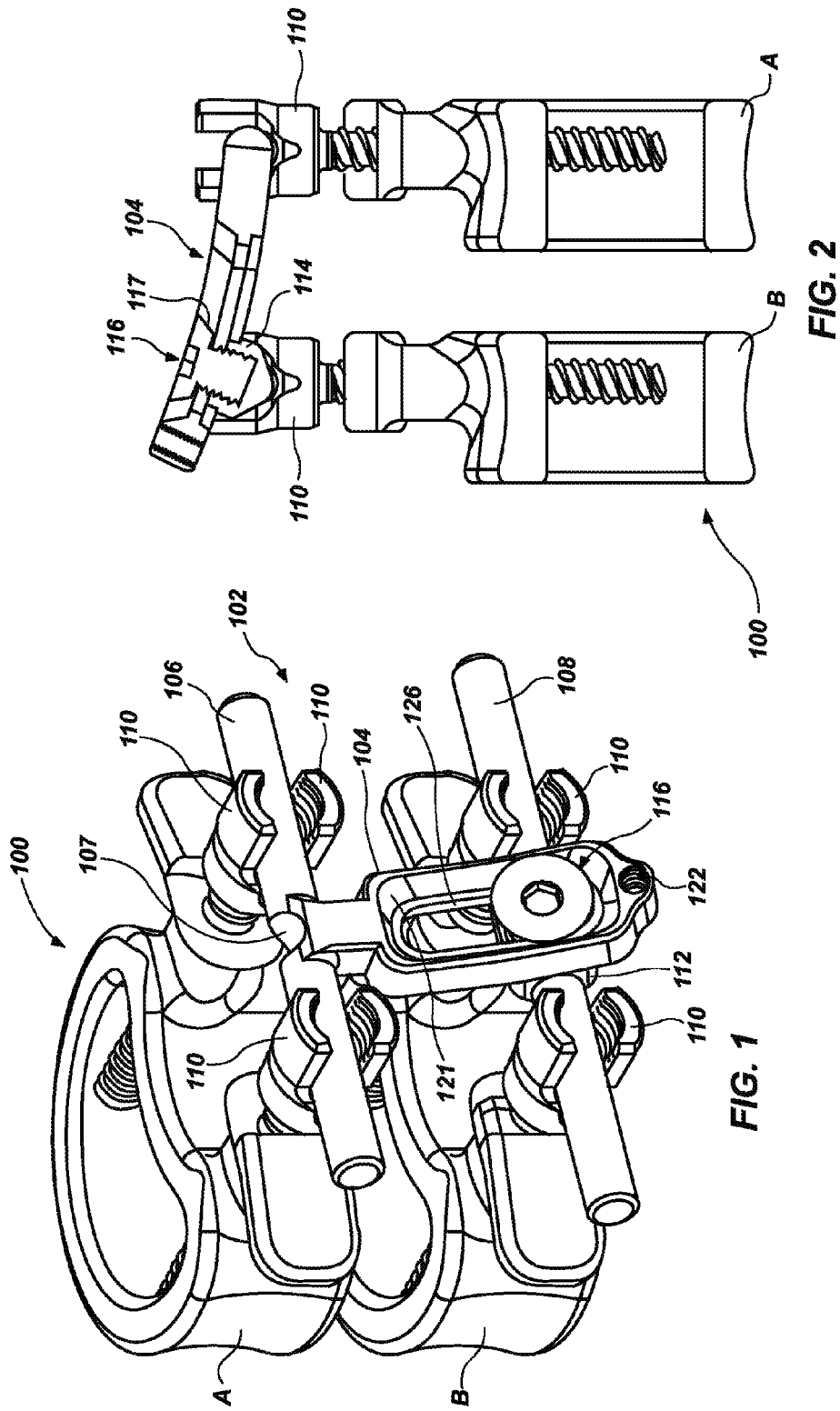

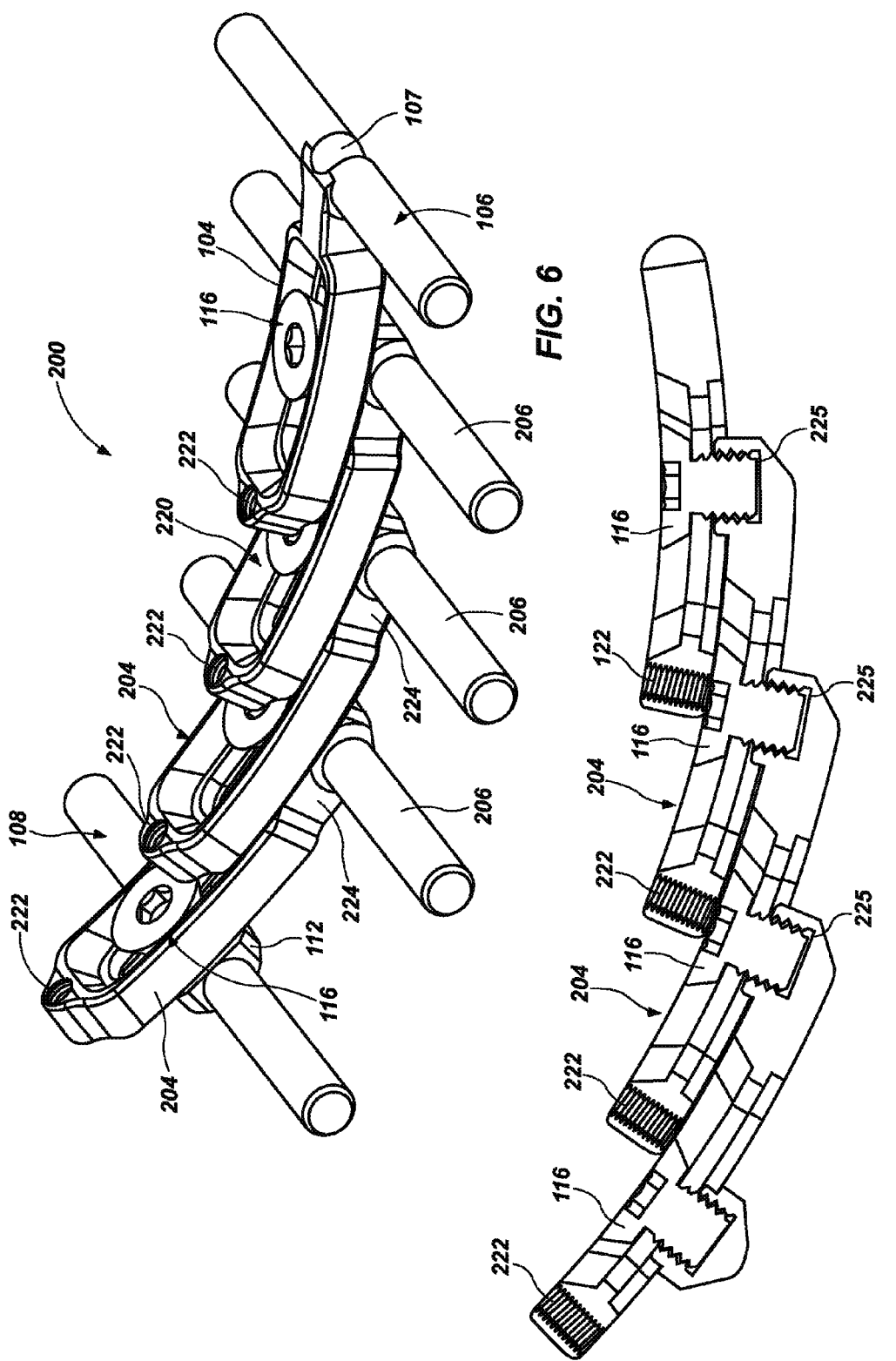

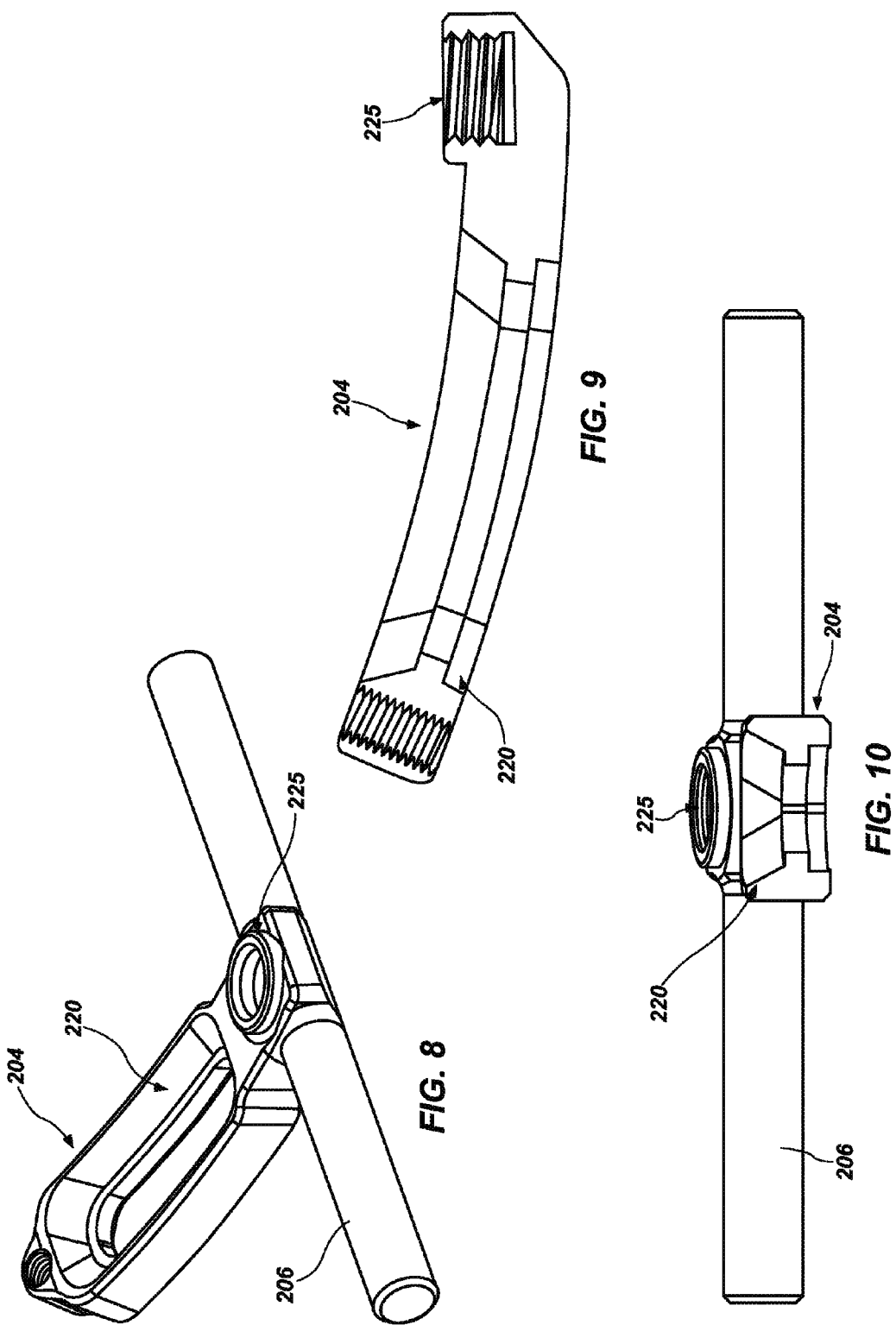

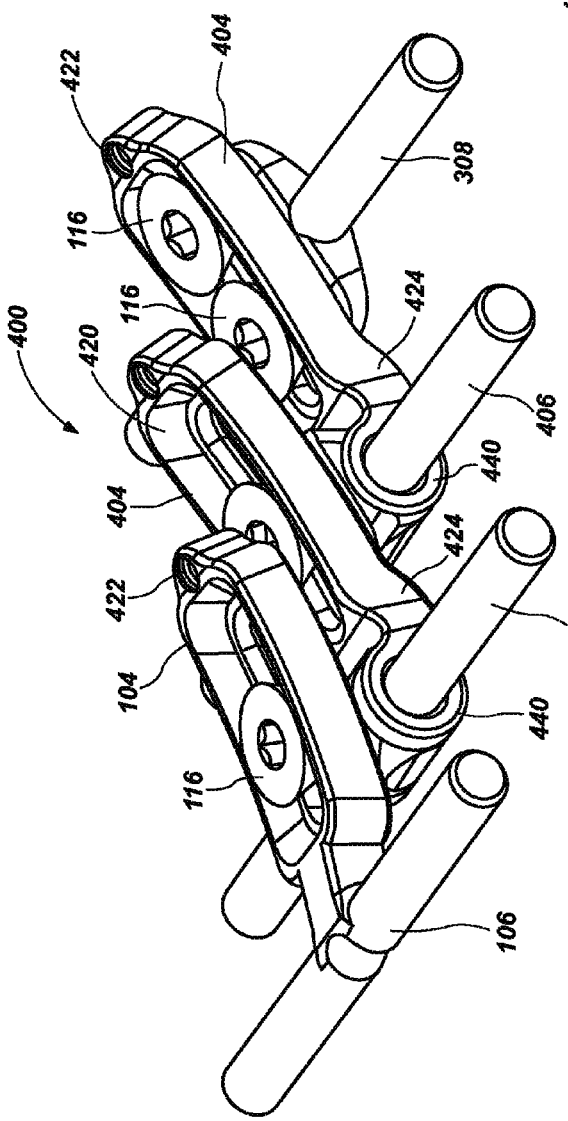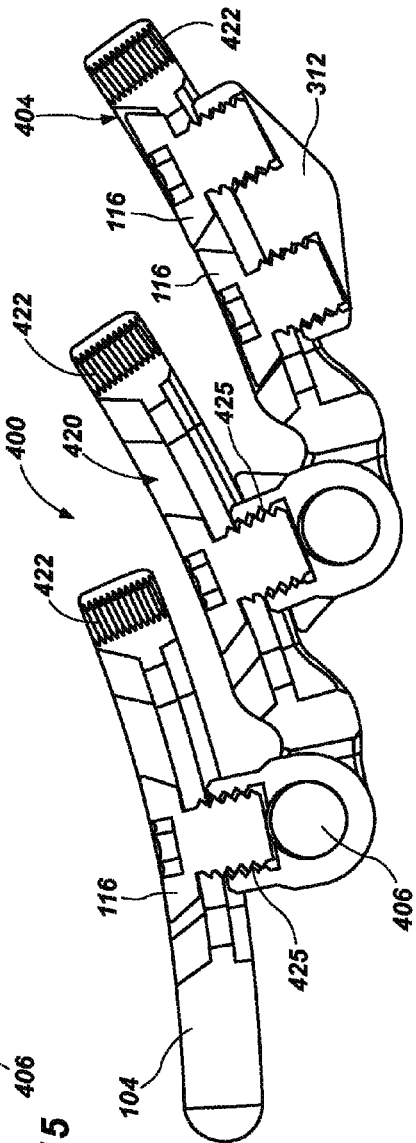

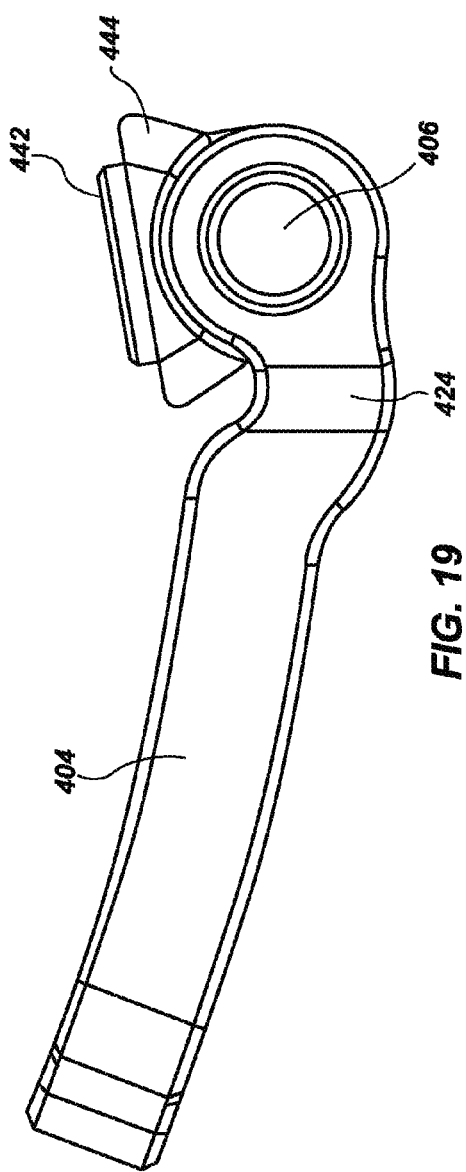
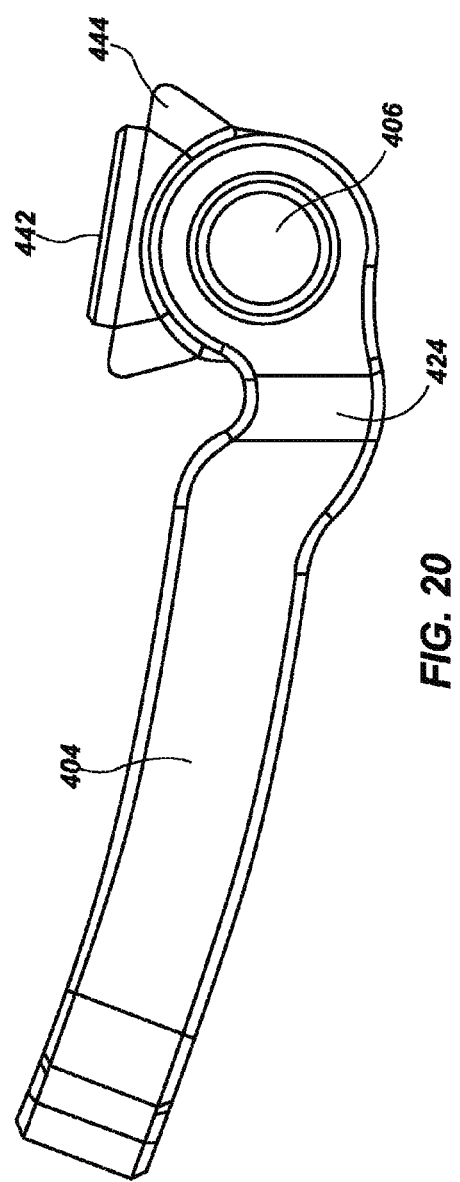

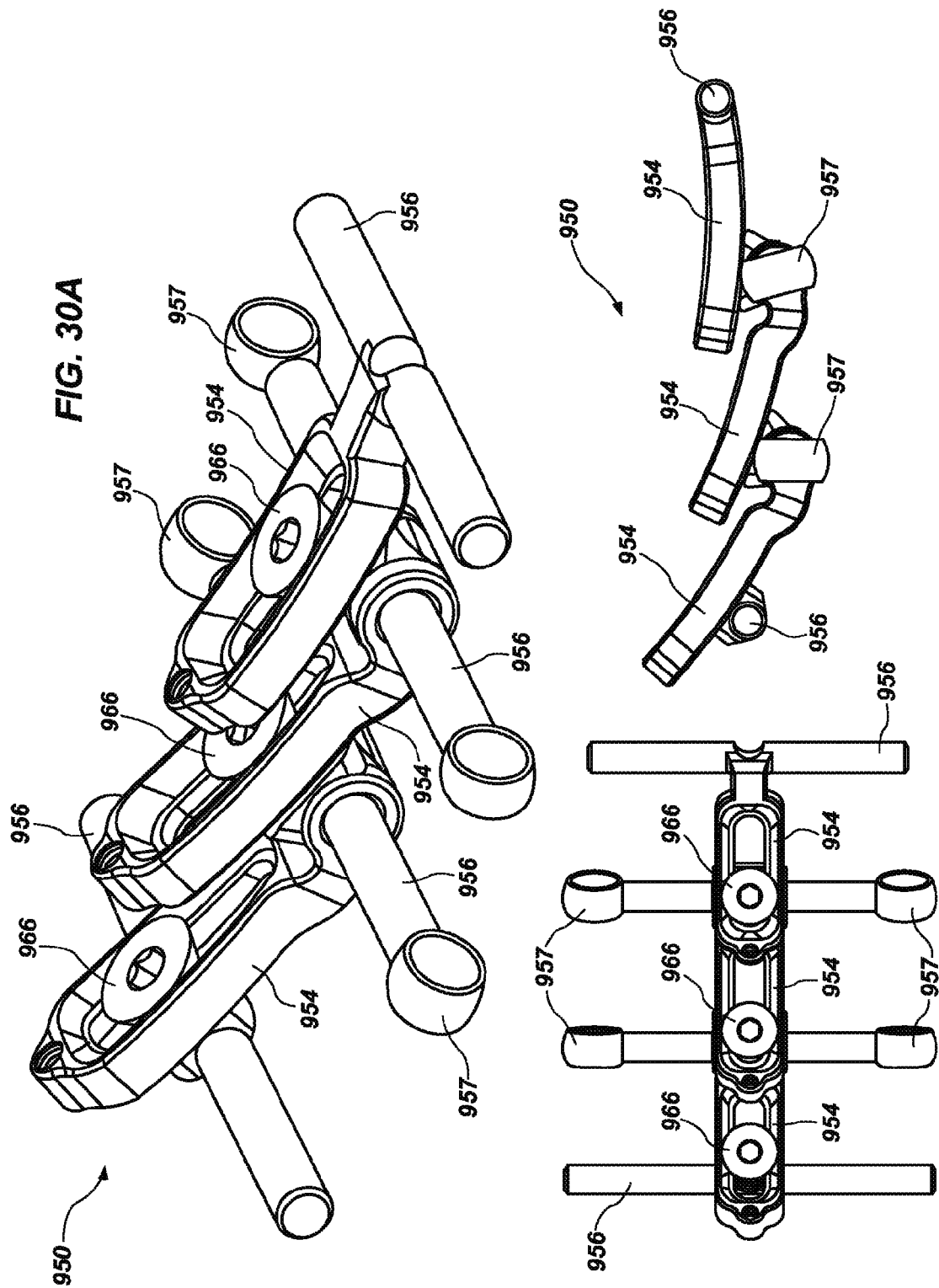

SEGMENTAL CORRECTION OF LUMBAR LORDOSIS

CROSS-REFERENCE TO RELATED APPLICATIONS

This application is a continuation-in-part of U.S. patent application Ser. No. 14/045,709 filed on Oct. 3, 2013, which is a continuation of U.S. patent application Ser. No. 13/869,855 filed on Apr. 24, 2013, which claims the benefit of U.S. Provisional Application No. 61/637,650 filed on Apr. 24, 2012, and this application also claims the benefit of U.S. Provisional Application No. 61/884,803 filed on Sep. 30, 2013, all of which are hereby incorporated by reference herein in their entireties, including but not limited to those portions that specifically appear hereinafter, the incorporation by reference being made with the following exception: In the event that any portion of the above-referenced applications is inconsistent with this application, this application supercedes said above-referenced applications.

STATEMENT REGARDING FEDERALLY SPONSORED RESEARCH OR DEVELOPMENT

Not Applicable.

BACKGROUND

1. The Field of the Present Disclosure.

The present disclosure relates generally to spinal stabilization devices.

2. Description of Related Art

Spinal fusion is surgery to permanently connect two or more vertebrae in a spine, eliminating motion between them. Spinal fusion may improve stability, correct a deformity or reduce pain. Spinal fusion may involve placing extra bone (bone graft) to fill the space between two spinal vertebrae. The bone graft material used in spinal fusion may be in a preformed shape, or it may be contained within a plastic, carbon fiber or metal cage. A surgeon may use plates, screws or rods to hold the vertebrae and graft in place to promote healing after spinal fusion. Once the bone graft heals, the vertebrae are permanently connected.

Longitudinal members that connect bony anchors in the spine are well known in the art for use in spinal fusion. These may connect multiple level anchors. Typically, two longitudinal members are utilized between each level, one on each side of the spinous process. Adjustable length transverse connectors are also known that connect longitudinal members to reduce motion between the roughly parallel longitudinal members. However, these prior art devices are characterized by being overly complex and in need of simplification.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 1 is a posterior view of a spine having an embodiment of the present disclosure installed thereon;

FIG. 2 is a cross-sectional side view of the spine and embodiment shown in FIG. 1;

FIG. 6 is a side view of an embodiment of the present disclosure;

FIG. 7 is a side cross-sectional view of the embodiment of FIG. 6;

FIG. 8 is a perspective view of an embodiment of the present disclosure;

FIG. 9 is a side cross-sectional view of the embodiment of FIG. 8;

FIG. 10 is a front cross-sectional view of the embodiment of FIG. 8;

FIG. 15 is a perspective view of an embodiment of the present disclosure;

FIG. 16 is a side cross-sectional view of the embodiment of FIG. 15; and

FIG. 19 is a side view of the embodiment of FIG. 17.

FIG. 20 is an alternative side view of the embodiment of FIG. 17.

FIG. 24b is an alternative side view of the embodiment of FIG. 24a.

FIG. 25b is an alternative side view of the embodiment of FIG. 24a.

FIG. 30A is a perspective, side and top view of an embodiment of the present disclosure.

DETAILED DESCRIPTION

Figure 3:
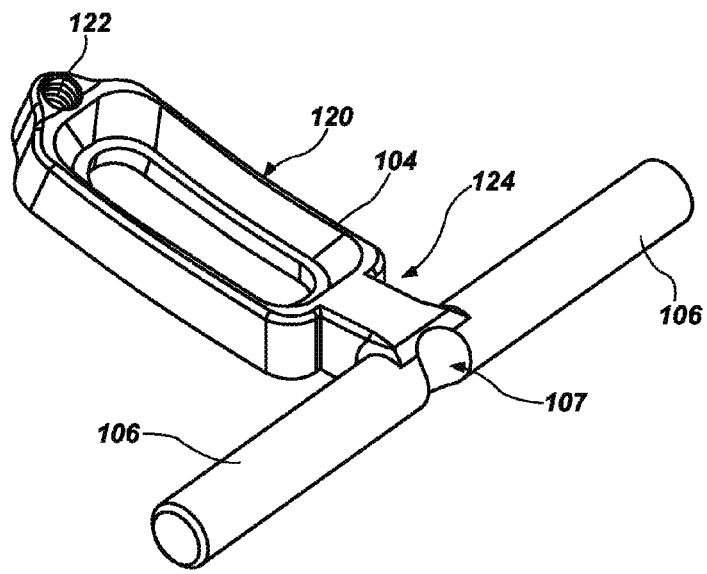
FIG. 3 is a perspective view of the embodiment shown in FIG. 1.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

Applicant has discovered a novel apparatus and method for aligning, stabilizing and securing the position of adjacent spinal vertebrae as part of a surgical procedure on a spine. Applicant's apparatus may comprise multiple levels of transverse members, each of which may be secured to a vertebra by multiple, or a pair of, anchoring devices. In an exemplary embodiment, a single longitudinal member may extend between each level of transverse members. The longitudinal member may be unitary or segmented across the different levels. Connectors may be utilized to join the segmented longitudinal member across the different levels of transverse members and to join the longitudinal member to the transverse members.

The Applicant's invention may be characterized by two or more anchors in the same vertebra that are utilized to secure a transverse member roughly in the transverse axis of the vertebra. The transverse member may take any one of a variety of shapes, including straight, convex or concave, telescoping, bent, and having generally perpendicular end members. The transverse members may be installed onto adjacent vertebrae. Adjacent transverse members may be joined by at least one longitudinal member, roughly in the midline of the spinal column or slightly offset from the midline. Connectors for securing a transverse member to a vertebra may include any suitable bone anchors, including pedicle screws, in both conventional and cortical position, lamina hooks or lamina screws or other bony fixation devices.

In an embodiment, a single level integrated transverse/longitudinal member connects to a similar construct at neighboring levels thus forming a multi-segmented plate. Multiple single level integrated transverse/longitudinal members may be connected to extend to multiple levels. The integrated transverse/longitudinal members may overlap like roof tiles. The integrated transverse/longitudinal members may be individually connected by a connection that allows engagement in a variety of relative positions, e.g., a polyaxial tulip with a rod or plate, but which can lock securely. This may allow easy connection of elements but then after repositioning of vertebrae using tools attached to the longitudinal or transverse members, the connection can be locked to secure the position.

The connections between longitudinal and transverse members may also allow engagement loosely to facilitate engagement but as tightening occurs, the members are forced into the desired position. Either method allows system to be used to position vertebrae as desired, especially for lordotic correction.

Respective adjacent transverse members or integrated transverse/longitudinal members may be loosely connected but not fully locked in a manner to allow sliding and adjustment, to thereby allow compression or distraction of the spinal segment. If there is a pivot point anterior to this connection, e.g., after insertion of an interbody cage as an earlier part of the procedure, then compression creates lordosis which is generally desirable in a fusion device. Conventional systems can also do this and during compression the vertebrae slide together along the fixed longitudinal rods to create lordosis.

However, vertebral antero or retrolisthesis is an anatomically normal part of the motion of the respective vertebrae during spinal flexion and extension. This is required anatomically in the lumbar spine because of the shape of the facet joint, but is not yet widely appreciated. In flexion, the superior vertebrae moves into anterolisthesis and in extension moves into retrolisthesis. This additional motion is not permitted in traditional methods of compression of the above conventional dual rods systems which may explain why they are poor at obtaining lordosis.

It is envisaged that the bone anchors used in this system may be locked in position, to help move the vertebrae but still allow rotation of the transverse members. By virtue of the transverse members ability to rotate within such a bone anchor, the present disclosure allows rotation about a transverse axis between adjacent transverse members during compression and thus retrolisthesis to occur during compression. This is an important advantage of this system over conventional. The system also incorporates embodiments that allow substantially the same relative motion (i.e. rotation between links and anchors) when used with bone anchors that do not allow rotation of the transverse member when the anchor is locked. These embodiments can allow lockable rotation between the transverse member and a link. This configuration has clinical value because it can enable a system to effectively work with substantially all types of bone anchors.

Both the transverse members, integrated transverse/longitudinal members and longitudinal members may contain features that can be connected to tools that by application of force to the spinal vertebrae via the anchored member reposition the vertebrae relative to its neighbor. Thus, individual plates and multiple plates may be used to correct a deformity in the spine. It is also envisaged that multiple spinal levels may be connected using a longitudinal member, having multiple segments aligned on a common axis, that connects to multiple transverse members. The system could also be used to connect a deformable or flexible longitudinal member thus creating a dynamic stabilizing device. In an embodiment, a segment of the longitudinal member can rotate about the longitudinal axis of adjacent transverse members.

In an embodiment, bone anchors may include standard pedicle screws with a standard polyaxial tulip allowing connection of a standard sized rod, e.g., 5.5 mm. These tulips accommodate the lateral parts of transverse members which are rods. Pedicle screws may be placed conventionally or cortically, preferably at least superior screws are placed in more medial cortical position In an embodiment, a longitudinal member may comprise a link or segment having an elongated through-hole or slot extending in the longitudinal direction of the link. The link may engage adjacent links via a bolt that extends through the slot of the link and is received by a threaded hole in the link of the adjacent link, thus fixing the two links together. The interior side surfaces the slot of the link may be sloped to facilitate smoother connection between the bolt and the link. The sloped interior surfaces of the slot also enable a looser initial connection between the bolt and the link, and thereby, provide gradual alignment of adjacent links during fixing engagement. The links of the longitudinal member may be convex to facilitate desired lordosis of the spine. It may be helpful to a have tool to help facilitate the bending of the links.

Eyebolt tulip: This has either a fixed, mono or polyaxial tulip that slides or clips over a transverse member to support a rod as part of a secondary longitudinal member.

In an embodiment, transverse members may have a channel or slot for receiving and confining a longitudinal portion of an adjacent transverse member. In an embodiment, a longitudinal member may comprise a long plate that can be bent in one plane only to fit lordosis. The long plate may fit into slot or channel on a transverse member. In an embodiment, washers may be utilized to help seat longitudinal members into connectors. It may be helpful to a have tool to help template plate bends, and method of bending so that plate is easily bent to fit.

In an embodiment, it may be easy to connect a rod between two polyaxial tulips screws. In effect, this transverse member may have rod pieces that easily engage tulips of bone anchors. Once a transverse member is inserted, the polyaxial heads can be used to align the transverse member in a desired position, e.g., parallel to its neighbour to facilitate fixation in situ, (to avoid any stress on screws) or if positional correction is desired, transverse members are positioned at a desired angle and the transverse members are manipulated.

In an embodiment, transverse members are fixed to pedicle screws at adjacent levels, and tools are then used to adjust position of adjacent transverse rods to desired position which is then secured by fixing a longitudinal member.

It will be appreciated that the present disclosure may allow ease of positional correction. This is because joining the bony anchors of one vertebrae into a single connection creates a single attachment point for tools to control positioning of the vertebra thus moving the vertebrae in a simplified manner compared to other available systems which engage left and right bone anchors separately rather than as one unit. Having adjusted and positioned the vertebrae relative to its neighbor, this position can then be fixed using the single or segmented longitudinal member which simplifies fixation compared to traditional anchor systems using dual longitudinal connectors. Such a mechanism will particularly aid in achieving the correction of lordosis and kyphosis. Rotational deformities in an axial plane of the spine are also correctable with this system because of the ease of pushing down on one side of the transverse member while pulling up on the other side of the transverse, which can efficiently control the position of an axially rotated segment, as can occur with scoliosis, for example. Although all other deformities maybe corrected.

It will be appreciated that a midline longitudinal member as described herein will have greater efficiency and advantage in creating lordosis and in its ability to resist flexion and extension. The advantage comes because the connection between pedicle screws provides a more posterior connection for tools than traditional pedicle screws systems and hence has a longer lever arm. Traditional dual lateral connector systems are very poor at creating lordosis as the screw tulips sit close to the pivot point. Recent knowledge has taught that lordosis is key to avoid adjacent segment disease and improved long term outcomes.

It will be appreciated that the present disclosure makes a good partner for a lateral cage, which is inherently stable implant whose only biomechanical weakness is in extension, which is maximally resisted by this device.

It will be appreciated that deformity can be corrected by adding single segment longitudinal links, link by link. Using such multiple longitudinal links avoids current alternative where rods often have to be bent to fit to screws. This bending weakens the rods and it can be difficult to fit the rods exactly to screws, requiring rods to be forced which has been shown to weaken screw bone interface which may predispose to screw loosening, pull out, loss of fixation which results clinically in failure to gain fusion and painful pseudoarthrosis. Multiple anchor points in a vertebrae spread any deformity correction forces used to manipulate the position of the vertebrae across multiple points of bony fixation in the vertebral body avoiding excessive stress when single bone screws are used sequentially.

Referring now to FIGS. 1 and 2, there is depicted partial views of a posterior portion of a spinal column 100. The spinal column 100 may include vertebrae, including vertebrae A and B as shown in FIG. 1. Each of the vertebrae A and B may include a spinous process as is known to one having ordinary skill in the art. Installed onto the spinal column 100 may be a stabilization apparatus 102. The apparatus 102 may comprise a longitudinal link 104 extending parallel to the spinal column 100 and along a centerline of the spinal column 100.

The apparatus 102 may further comprise a plurality of transverse rods 106 and 108. Transverse rod 106 may be attached to vertebra A by a pair of polyaxial tulip head screws 110. The transverse rod 106 may be substantially perpendicular to the spinal column 100 and the longitudinal link 104. Transverse rod 108 may be attached to vertebra B by a pair of polyaxial tulip head screws 110. The transverse rod 108 may be substantial perpendicular to the spinal column 100 and the longitudinal link 104.

Each of the screws 110 securing the transverse rods 106 and 108 may have a cortical trajectory or medial to lateral trajectory. Transverse rod 106 may be fixed to the longitudinal link 104 to substantially prevent translational, toward or away from, or pivotal movement there between. Transverse rod 106 may also include a concave groove 107 that may be used to accommodate a superior spinous process (not shown).

A connector 112 may be integral or fixed to transverse rod 108 and may be utilized to join the longitudinal link 104 to transverse rod 108. Connector 112 may include a threaded bore 114 that may receive a bolt 116, or other desired fastener. The bolt 116 can pass through an elongated through-hole 120, formed in the longitudinal link 104, and threadedly engage bore 114. As bolt 116 is securely fasted to bore 114, longitudinal link 104 can become translationally and pivotally fixed to transverse rod 108. The phrase "translationally fixed" as used herein, such as a first member being translationally fixed to a second member, shall mean that the first member cannot move in translation with respect to the second member (medially, laterally, longitudinally or in other non-rotational or translational motions), with the understanding that the phrase "translationally fixed" does not mean that the first member cannot move rotationally with respect to the second member. For example, the longitudinal link 104 being translationally fixed relative to transverse rod 108, means the longitudinal link 104 cannot move in translational motion relative to transverse rod 108, or vice versa. The elongated through-hole 120 enables movement between transverse rods 106 and 108 after initial connection of the bolt 116 into bore 114, but before the bolt is firmly seated within the bore.

Elongated through-hole 120 may include sloped interior surface 121 that corresponds to a sloped exterior surface 117 on bolt 116. These corresponding surface 117 and 121 facilitate centering of the bolt 116 into the through-hole 120 during installation and positional adjustments. A surgeon may fine tune the positioning of transverse rods 106 and 108 by increasing or decreasing engagement of the bolt 116 within the bore 114. The through-hole of the link 104 may extend more half the length of the link 104 to increase the range of mobility between transverse rods 106 and 108. The ratio of the width of the link 104 to the length of the link 104 can range from substantially 0.25-0.5, for example, depending on the type of link being used and the type deformity or injury being corrected. Longitudinal link 104 may also include a threaded bore 122 that may receive a spinous process stud (not shown) to provide an anchor point for suturing (or other methods of reconnecting) midline soft tissues in order to recreate a posterior tension band that may have become disrupted by exposure of the wound created during implantation of the disclosed device. The spinous process stud may be shaped as a post or, alternatively, as a fin or plate, for example.

Figure 4:
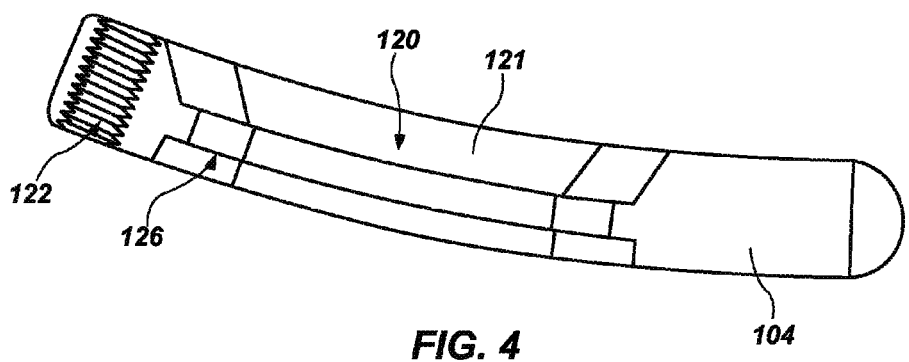
FIG. 4 is a cross-sectional view of the embodiment of the present disclosure.
Figure 5:
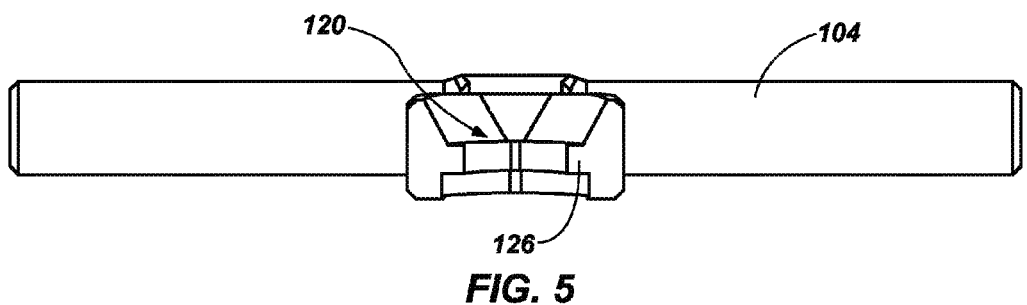
FIG. 5 is a posterior view of an embodiment of the present disclosure.

FIGS. 3-5 depict the longitudinal link 104, isolated with transverse rod 106. As shown in FIG. 3, a bridge 124 connects the transverse rod 106 with longitudinal link 104. Bridge 124 may have substantially the same thickness as link 104, however, bridge 124 may have a reduced width to potentially accommodate narrowly spaced bone anchors, such as screws 110.

FIG. 4 illustrates a convex curvature of the link 104, which can facilitate proper lordosis of the spine 100 by securing adjacent vertebra in a corresponding curvature.

As shown in FIGS. 4 and 5, link 104 includes a flange 126 on the interior surface of through-hole 120. Flange 126 may extend perpendicularly to bolt 116, to prevent bolt 116 from over extending through the through-hole 120 during installation. The flange 126 may include portions that extend substantially parallel and others that extend substantially perpendicularly with respect to transverse rod 106.

FIGS. 6 and 7 illustrate a spinal stabilization apparatus 200 pursuant to an embodiment of the present disclosure. The apparatus 200 may include a plurality of transverse rods 106, 108 and 206. The transverse rods 106, 108, and 206 may be attached to separate vertebrae by polyaxial tulip head screws similar to what is shown in FIG. 1. The apparatus 200 may comprise a central connector that includes a plurality of longitudinal links 104 and 204 extending parallel to the spinal column and along a centerline of the spinal column. The links 104 and 204 may overlap immediately adjacent links similar to roof tiles or reptile scales. Each link 204 may have similar features as link 104 disclosed above, including convex shape, elongated through-hole 220 and interior through-hole geometry, and a bore 222 that may receive a spinous process anchor. Also similar to link 104, intermediate links 204 may be pivotally and translationally fixed to a transverse rod 206 via a bridge 224. However, intermediate links 204 can also include a threaded bore hole 225 that can receive a bolt 116 to connect adjacent links 104 and 204.

As shown in reference to link 104 and bridge 124 in FIG. 3 and link 204 and bridge 224 in FIG. 6, the bridge feature of the present disclosure includes an upper surface (shown in FIG. 3 but not labeled) and a lower surface (shown in FIG. 6 but not labeled), and the link feature is also shown as having upper and lower surfaces (shown but not labeled), and it will be understood that the upper surface and the lower surface of the bridge illustrate the concept of an extension surface of the upper surface of the link and an extension surface of the lower surface of the link, respectively, such that those extension surfaces extend along the same path or route or direction of said upper surface of the link and lower surface of the link, respectively, such that the transverse rod 106 resides entirely between imaginary extension surfaces extending from the upper and lower surfaces of the link and along the same path, route or direction of said upper and lower surfaces of the link, respectively. Since transverse rod 106 is shown in FIG. 3 and in FIG. 6 as residing between upper and lower surfaces of the bridge 104 and bridge 204, respectively, it is shown that the transverse rod 106 thereby also resides between imaginary extension surfaces extending from the upper and lower surfaces of the link and along the same path, route or direction of said upper and lower surfaces of the link, respectively.

To assemble the apparatus 200, an initial link 204 in the most superior position can be fixed to the transverse rod 108 via bolt 116. Each adjacent link is then overlapped and fixed to the immediately adjacent link 104 or 204 via a bolt 116 which passes through the through-hole 220 and is received by bore 225, as shown in FIG. 7.

FIGS. 8-10 illustrate additional views of intermediate links 204 and corresponding transverse roads 206.

Figure 12:
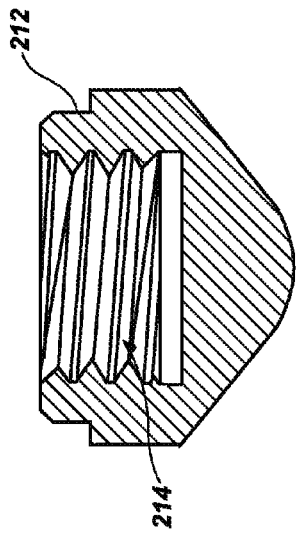
FIG. 12 is a side cross-sectional view of an embodiment of the present disclosure.
Figure 13:
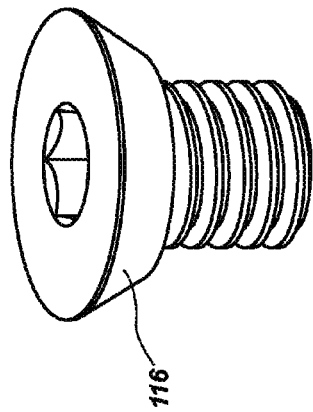
FIG. 13 is a perspective view of an embodiment of the present disclosure.
Figure 11:
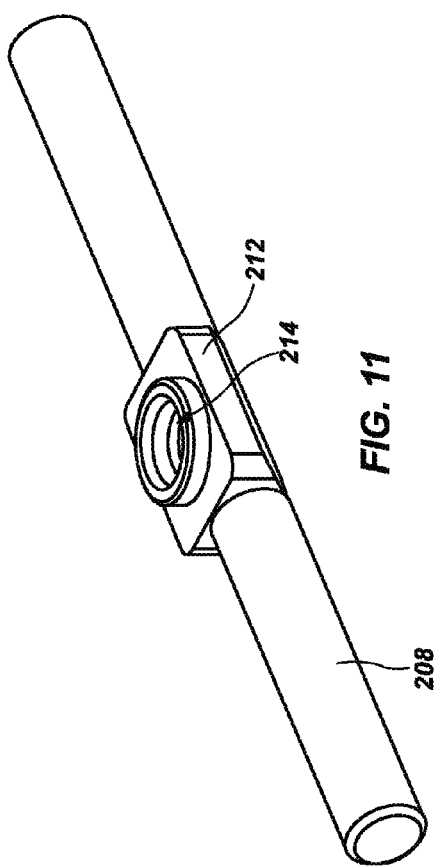
FIG. 11 is a perspective view of an embodiment of the present disclosure.

FIGS. 11-13 illustrate isolated views of transverse rod 208, connector 212 and a corresponding bolt 116.

Figure 14:
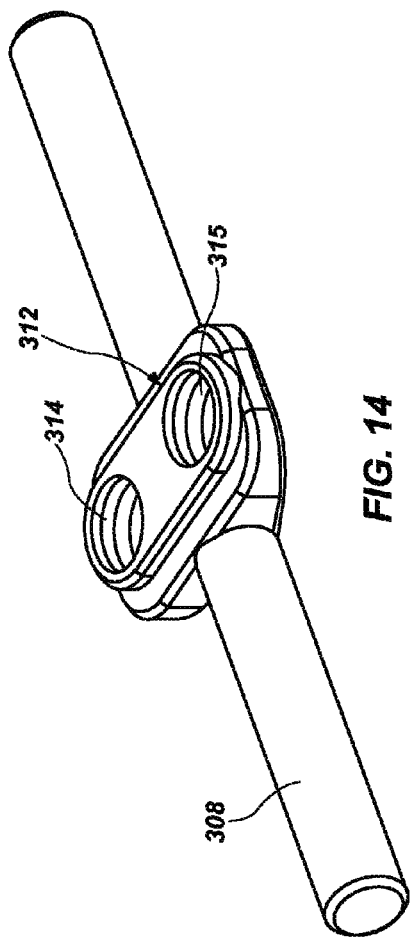
FIG. 14 is a perspective view of an embodiment of the present disclosure.
Figure 17:
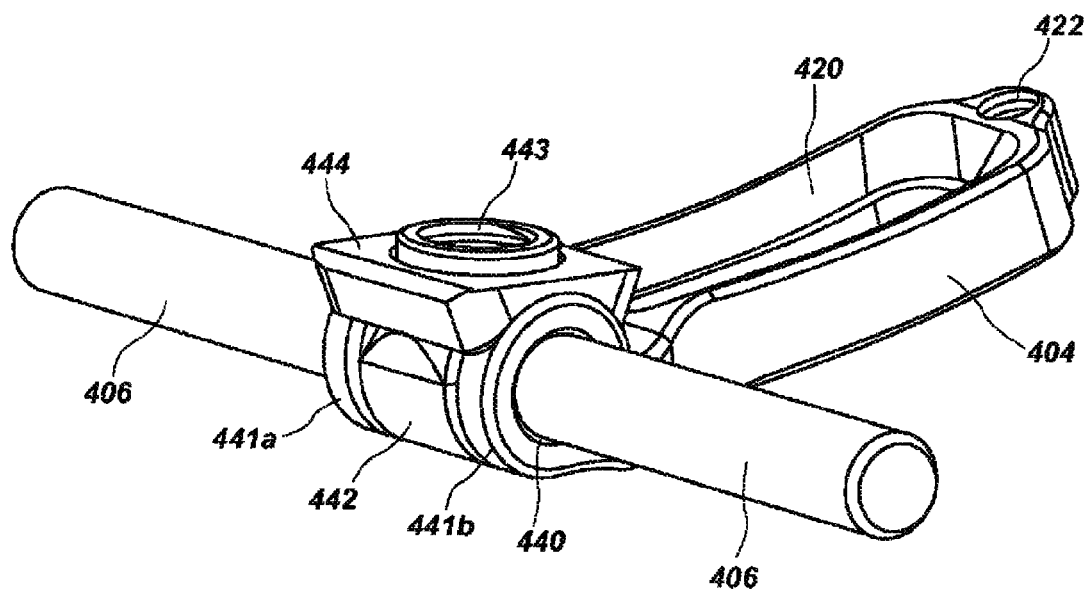
FIG. 17 is a perspective view of an embodiment of the present disclosure.
Figure 18:
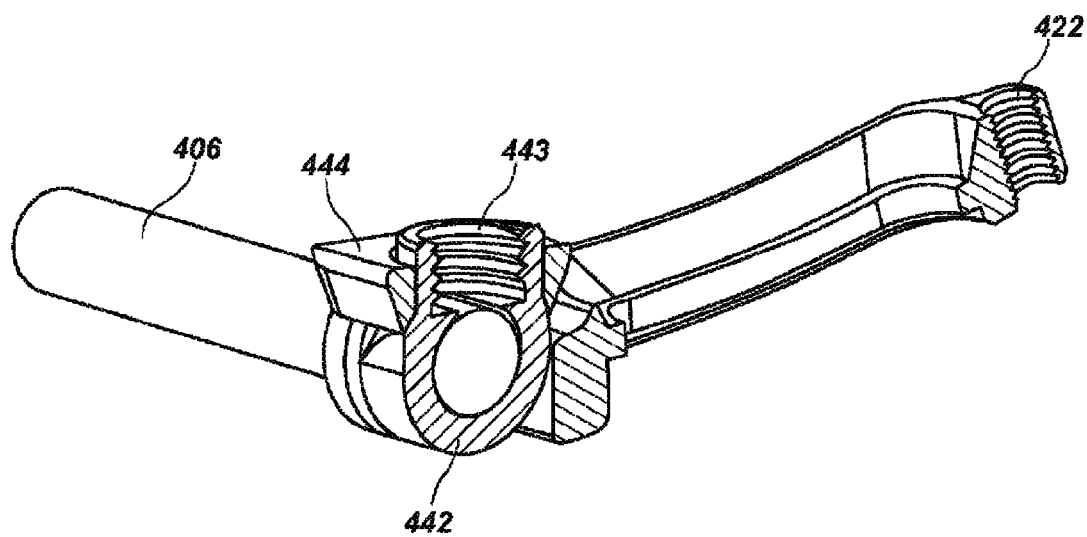
FIG. 18 is a perspective cross-sectional view of the embodiment of FIG. 17.
Figure 21:
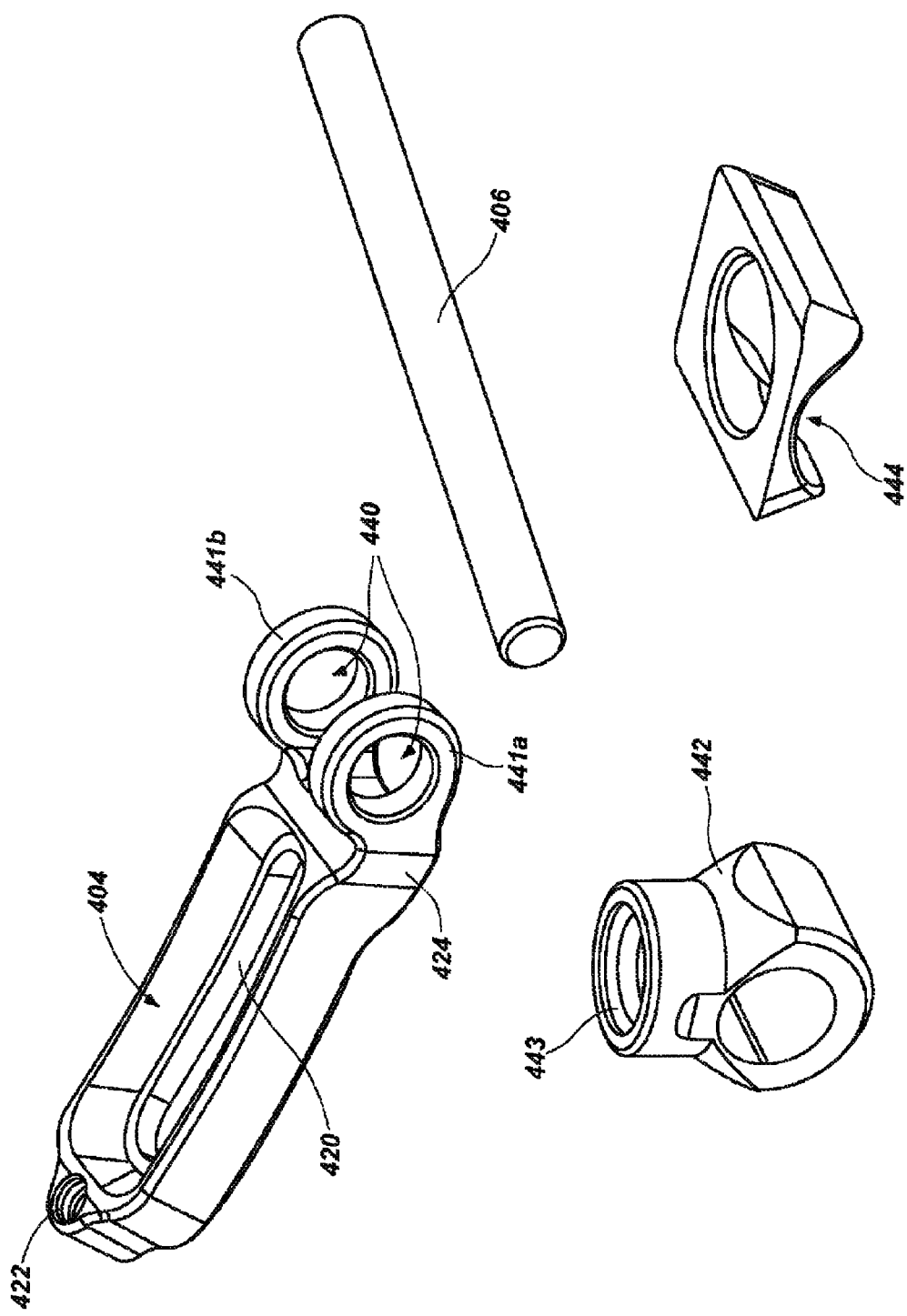
FIG. 21 is a perspective view of isolated elements of an embodiment of the present disclosure.

FIG. 14 illustrates an embodiment of the current disclosure that includes a transverse rod 308 that may be translationally and pivotally fixed to a connector 312. Connector 312 can include a first and second threaded bore 314 and 315 to receive corresponding bolts 116 to fix the position of a link 104 or 204 with respect to the transverse rod 308. Connector 312 having two bores 314 and 315 can add additional stability and securement to stabilizing apparatuses 102 and 200. If desired, transverse rod 308 can be used interchangeably with transverse rod 208 in apparatus 102 and 200.

FIGS. 15 and 16 illustrate a spinal stabilization apparatus 400 pursuant to an embodiment of the present disclosure. The apparatus 400 may include a plurality of transverse rods 106, 308 and 406. The transverse rods 106, 308, and 406 may be attached to separate vertebrae by polyaxial tulip head screws similar to what is shown in FIG. 1. The apparatus 400 may comprise a plurality of longitudinal links 104 and 404 extending parallel to the spinal column and along a centerline of the spinal column, similar to FIGS. 6 and 7. The links 104 and 404 may overlap immediately adjacent links. Each link 404 may have similar features as links 204 disclosed above, including convex shape, elongated through-hole 420 and interior through-hole geometry, and a bore 422 that may receive a spinous process anchor.

As opposed to links 104 and 204, links 404 are moveable with respect to corresponding transverse rods 406. The transverse rod 406 may freely pass freely through channel 440 which is attached to link 404 via a bridge 424, enabling the link 440 to pivot about transverse rod 406. Bridge 424 is similar to bridges 124 and 224, however, bridge 424 also includes a concave shape between the transverse rod 406 and the link 404. The concave geometry of the bridge 424 can enable a more flush engagement between adjacent links 404 that have different angles of trajectory with respect to corresponding transverse rods 406 and can allow a saddle 444 (discussed in more detail below) to rotate around a channel 440 to increase the range of alignment options for adjacent links. Also similar to intermediate links 204, links 404 can also include a threaded bore hole 425 that can receive a bolt 116 to connect adjacent links 104 and 404.

To assemble the apparatus 400, an initial link 404 in the most superior position can be fixed to the transverse rod 308 via bolts 116. Each adjacent link is then overlapped and fixed to the immediately adjacent link 104 or 404 via a bolt 116 which passes through the through-hole 420 and is received by bore 425, as shown in FIG. 16.

FIGS. 17-21 illustrate isolated views of link 404 and transverse rod 406. FIGS. 17-21 also illustrate the moveable connection between the link 404 and the transverse rod 406. Channel 440 is formed through hoops 441a and 441b, which can be integral with link 404. Channel 440 may include a central opening, between hoops 441a and 441b, to receive an eyelet 442 which can be pivotally engaged therewith. The eyelet 442 can receive transverse rod 406 and is pivotable therewith, until a bolt 116 is firmly secured within threaded bore 443. As the bolt 116 is tightened, downward pressure on the saddle 444 is transferred to hoops 441a and 441b, while simultaneously the eyelet pulls the transverse rod 406 upward towards the hoops 441a and 441b. These combined pressures can provide sufficient friction between the transverse rod 406 and the hoops 441a and 441b to substantially fix the transverse rod 406 against rotation with respect to the link 404. Alternatively, in another embodiment, as the bolt 116 can seat against the transverse rod 406 at the bottom of the bore 443 and the eyelet 442 can become pivotally fixed with respect to the transverse rod 406. Other embodiments, may include interlocking grooves between the eyelet 442, rod 406 or hoops 441a and 441b, or roughening a surface of the rod 406, eyelet 442 and/or hoops 441a and 441b to increase the relative friction between these element to improve fixing or locking capability.

The saddle 444 can be connected to the eyelet 442 about the bore 443. The saddle can provide additional stability between adjacent links connected via a bolt 116 secured within bore 443. Therefore, saddle 444 and eyelet 443 can pivot together with respect to the transverse rod 406, as shown in FIGS. 19 and 20, until the firm seating of the bolt 116 within the bore 443.

The pivotable links 404 and apparatus 400 enable a surgeon to accommodate a desired vertebral configuration that does not strictly adhere to the curvature of the links 404, or as shown with respect to the apparatus 200. Therefore, each adjacent link 104 or 404 may have a different angle or trajectory with respect to other adjacent links 104 or 404.

Figure 22:
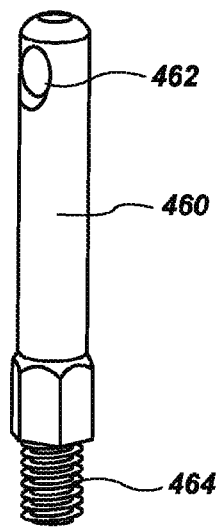
FIG. 22 is a perspective view an embodiment of the present disclosure.
Figure 23:
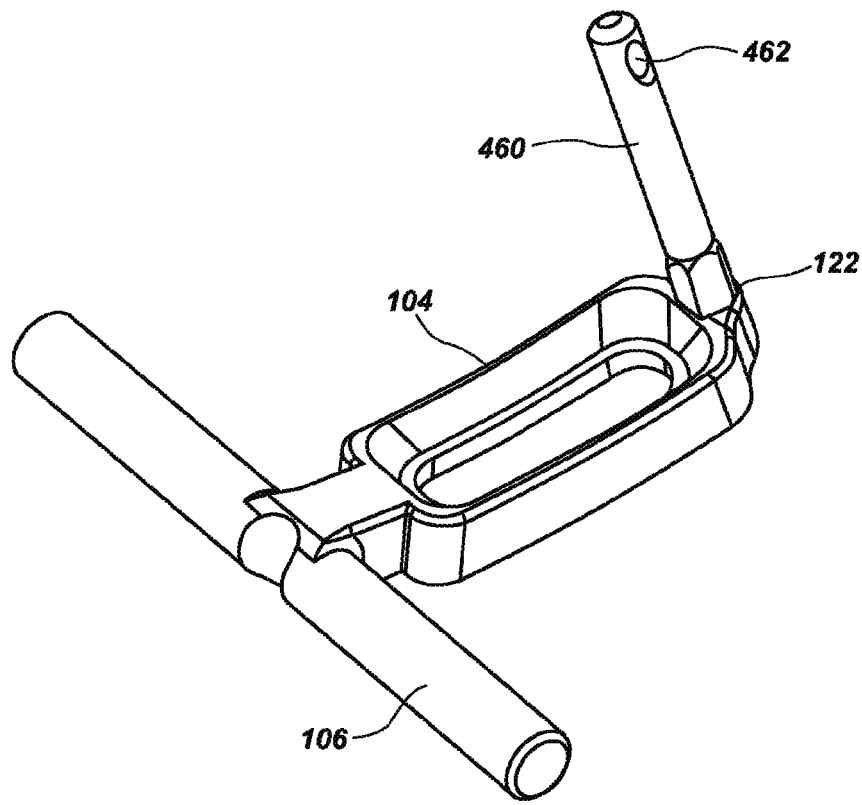
FIG. 23 is a perspective view of an embodiment of the present disclosure.

FIGS. 22 and 23 illustrate a spinous process anchor 460 of an embodiment of the current disclosure. Spinous process anchor 460 can be compatible with all previously disclosed links 104, 204 and 404 and may include an eyelet 462 for suturing tissue. Anchor 460 can include a threaded base to facilitate a threaded connection to link 104 via bore 122, or engaged to other similarly disclosed threaded bores 222 and 422.

Figure 24A:
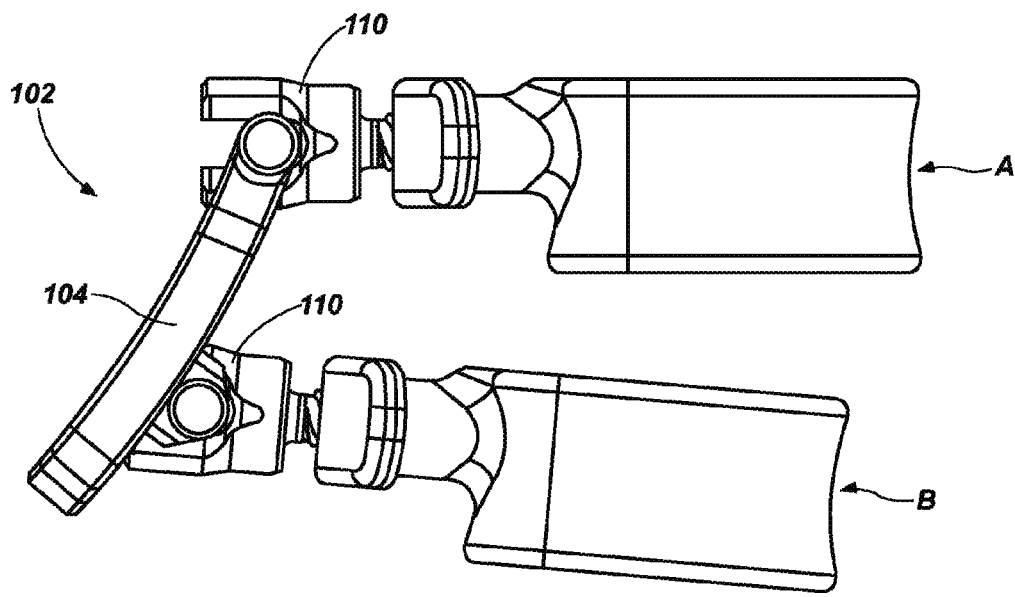
FIG. 24a is a side view of an embodiment of the present disclosure.
Figure 24B:
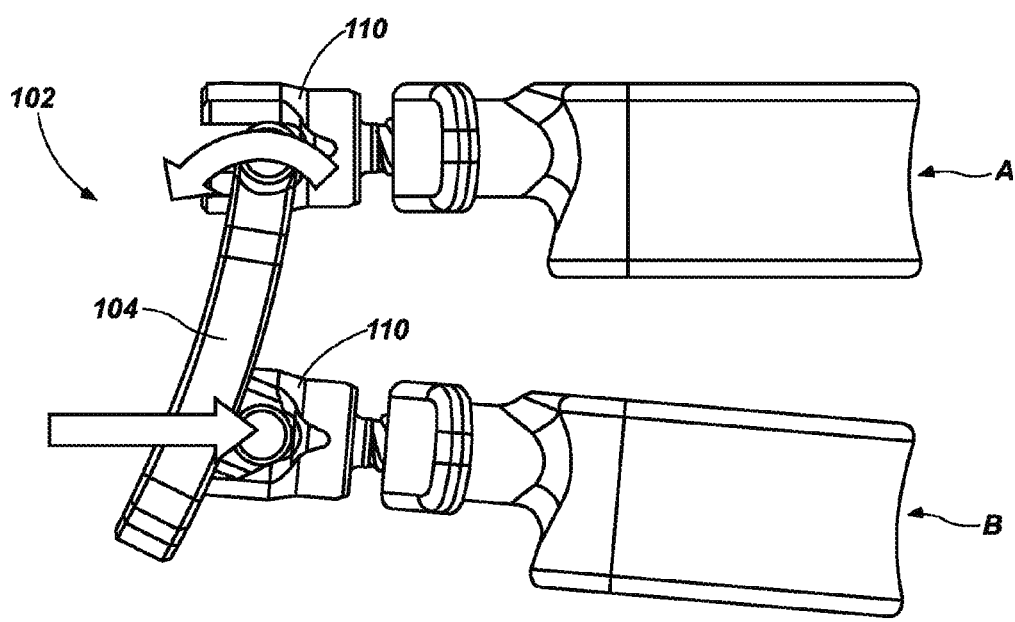

FIGS. 24a and 24b illustrate an exemplary method of using apparatus 102 to correct a spinal deformity according to an embodiment of the current disclosure. FIG. 24a illustrates an initial position of deformed vertebra A and B when initially secured to apparatus 102. FIG. 24b illustrates how pulling out on the superior level and pushing in on the inferior level of the apparatus can reduce spondylitic levels. A spine segment cage (not shown) can be present within the intervertebral space and can provide an anterior pivot point.

Figure 25A:
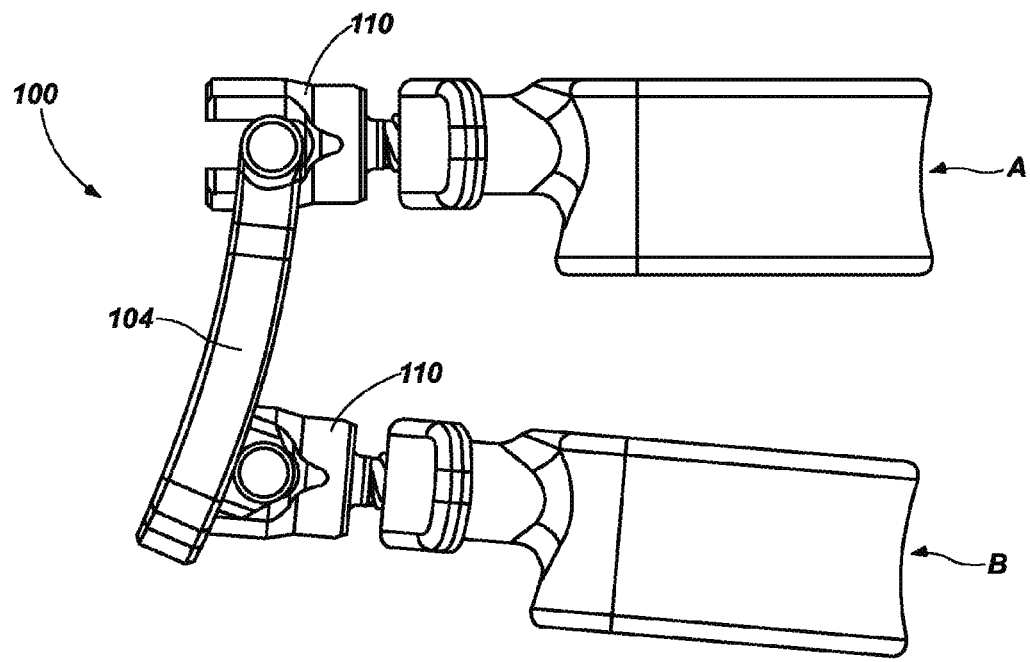
FIG. 25a is a side view of an embodiment of the present disclosure.
Figure 25B:
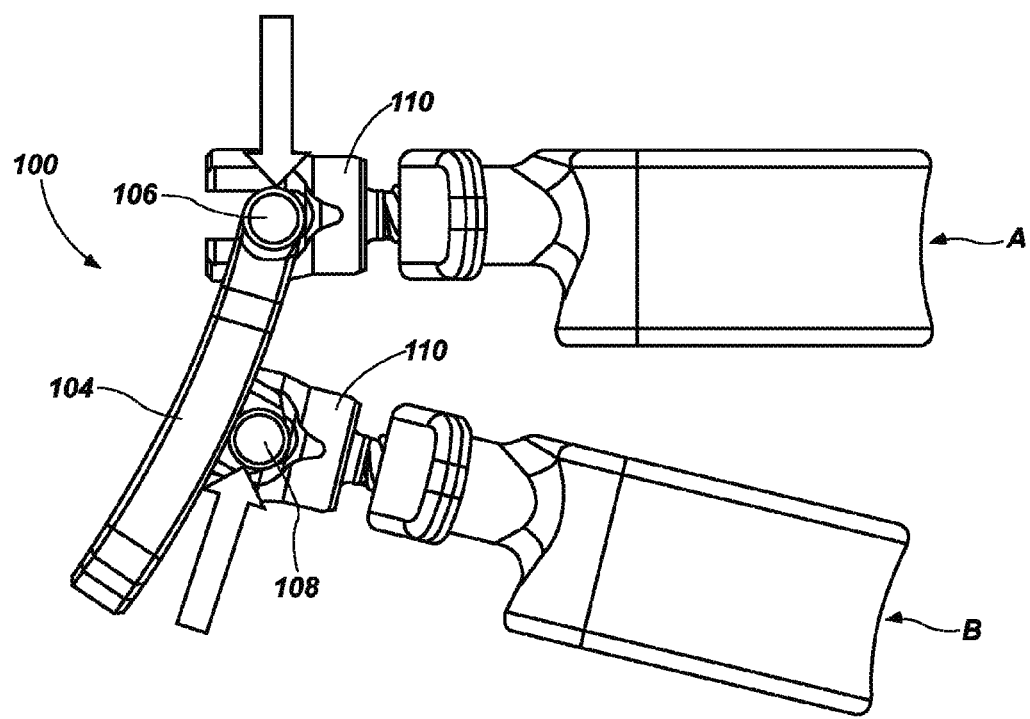

FIGS. 25a and 25b illustrate an exemplary method of using apparatus 102 to correct a spinal deformity according to an embodiment of the current disclosure. FIG. 25a illustrates an initial position of deformed vertebra A and B when initially secured to apparatus 102. FIG. 24b illustrates how compressing rods 106 and 108 posteriorly can induce lordosis in vertebrae A and B.

Figure 26:
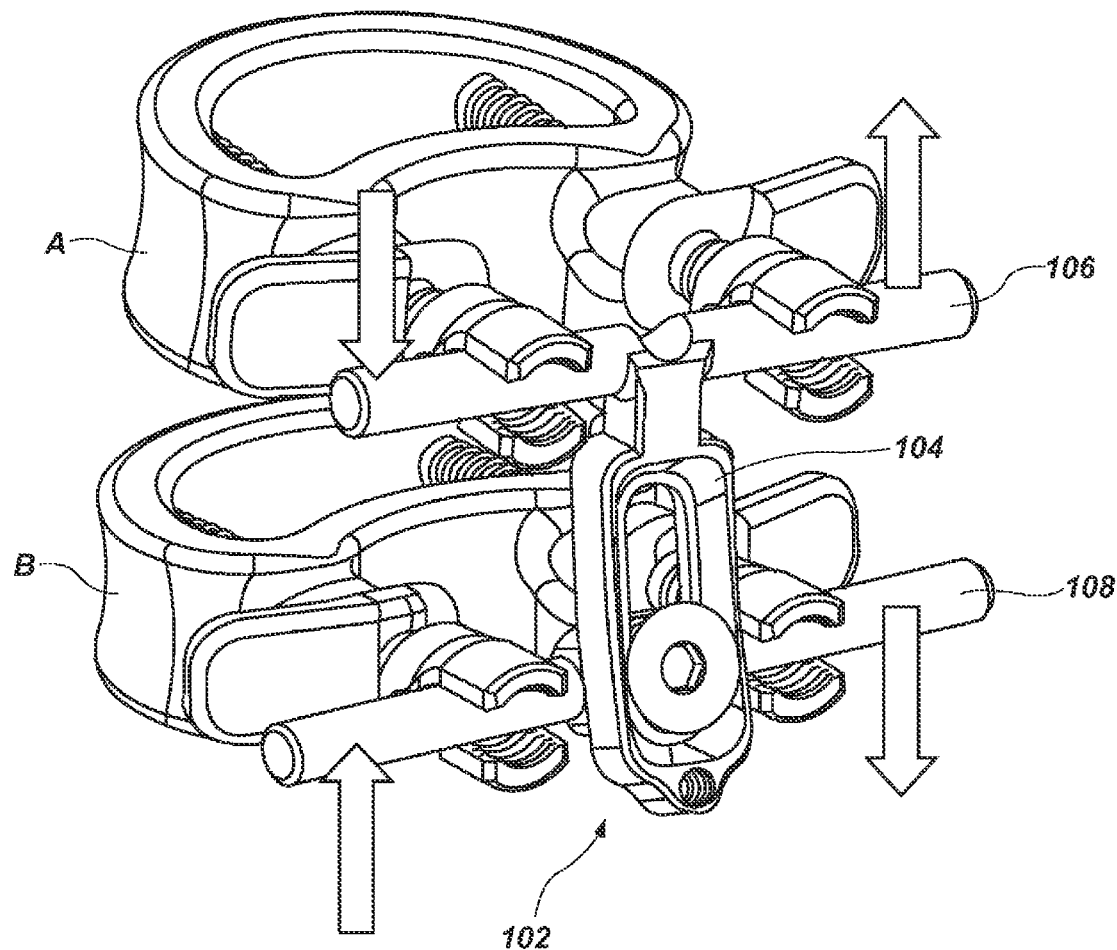
FIG. 26 is a perspective view of an embodiment of the present disclosure.

FIG. 26 illustrates an exemplary method of using apparatus 102 to correct a spinal deformity according to an embodiment of the current disclosure. FIG. 26 illustrates how compressing on corresponding ends of rods 106 and 108 while distracting opposing, and corresponding, ends of rods 106 and 108 can correct Coronal plane deformities. Similarly, although not illustrated, pushing an end of rod 106 forward and pulling an opposing end of rod 106 backward while simultaneously applying opposite forces to respective ends or rod 108 can apply rotational forces and allow correction of axial rotational deformities useful for scoliosis correction, for example. It is a useful feature of this system that deformities can be completely or partially corrected as desired. This disclosed system allows connection of adjacent links 104 and 404 with substantially the same or different longitudinal axis as desired.

Figure 27A:
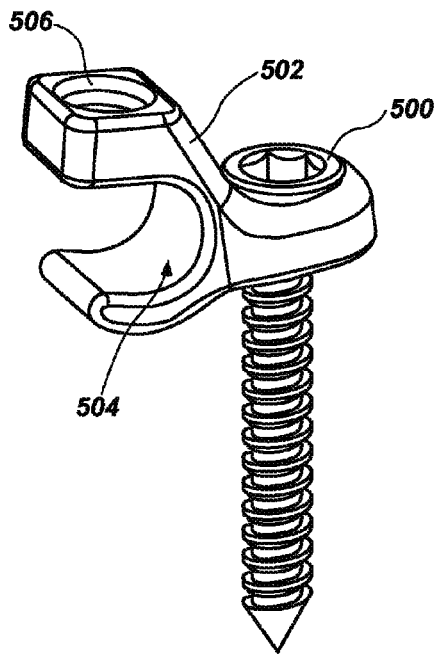
FIG. 27a is a perspective view of an embodiment of the present disclosure.
Figure 27B:
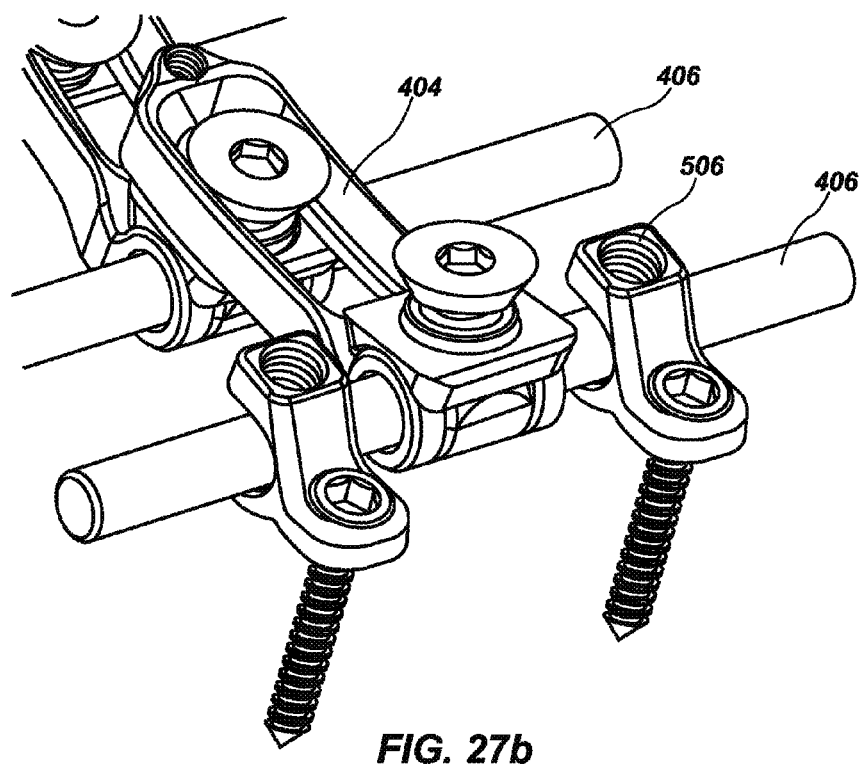
FIG. 27b is a perspective view of an embodiment of the present disclosure.

FIGS. 27a and 27b illustrate an facet screw 500 and connector 502 of an embodiment of the current disclosure. The facet screw can be used in place of tulip screws 110 disclosed above, to secure a transverse rod 406 to a corresponding vertebra (not shown). The facet screw 500 can be received by connector 502 and connector 502 can receive rod 406 within a concave portion 504 of the connector 502. Once the rod 406 is in a desired position a bolt 116 (not shown), or other desired fastener can be seated firmly within a threaded bore 506 and seated against the rod 406, securing the rod against rotation and translation with respect to the connector 502.

Figure 28:
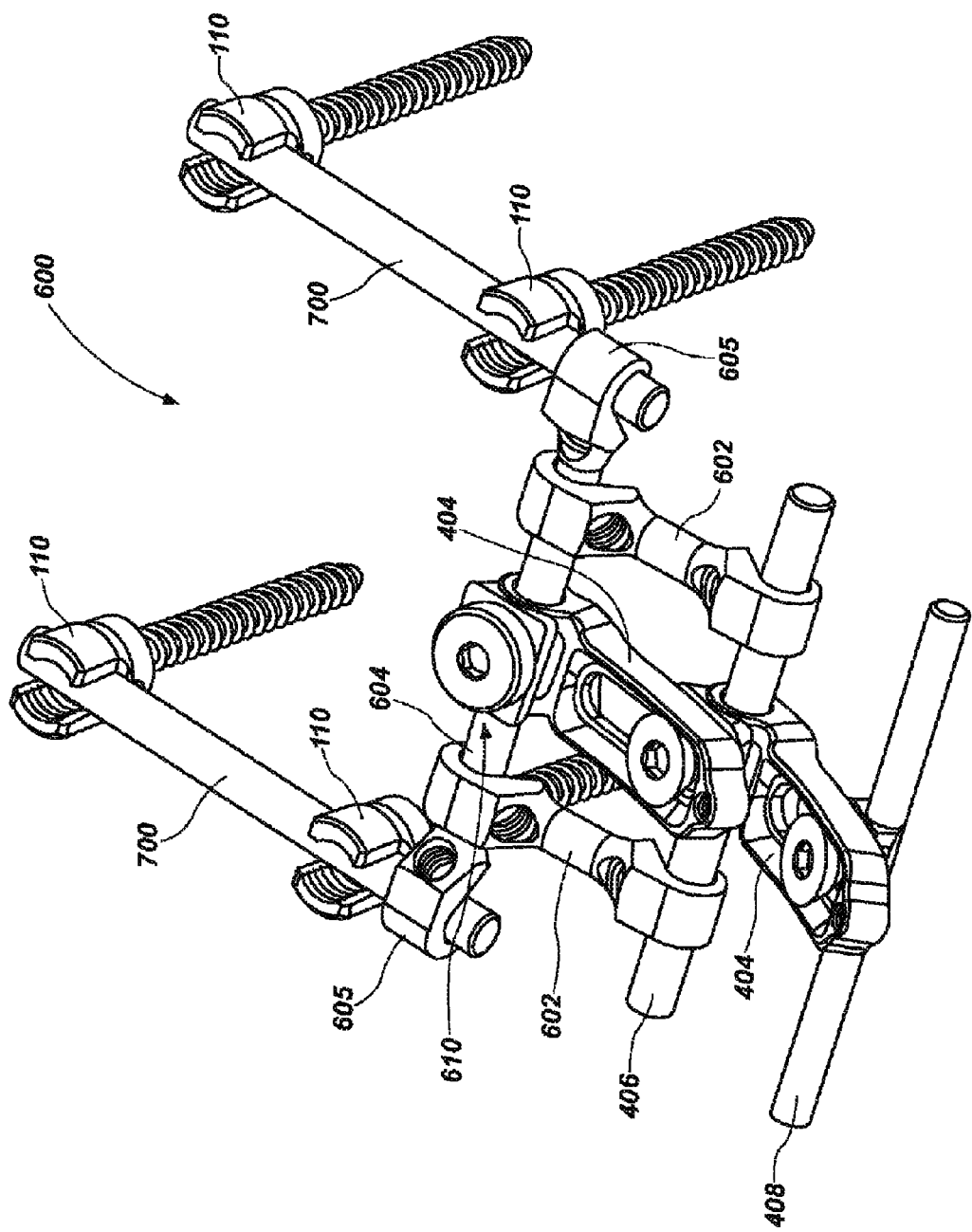
FIG. 28 is a perspective view of an embodiment of the present disclosure.

FIG. 28 illustrates a spine stabilizing apparatus 600 according to an embodiment of the current disclosure. The apparatus 600 can include links 404 and transverse rods 406 and 408 and can be secured and attached in a manner and configuration similar to apparatus 400. Apparatus 600 can include crosslinks 602 that can be used for additional lateral strength and stability. Crosslinks similar to crosslinks 602 may be used with assemblies 200 and 400 to connect respective transverse rods. An adapter rod 604 can be used in place of a transverse rod 404, for example, and can enable apparatus 600 to interface with a conventional longitudinal rod construct having parallel rods 700 secured to respective vertebrae (not shown) via tulip screws 110. The adapter rod 604 can include hook portions 605 on opposing terminating ends that can latch onto respective end portions of parallel rods 700. The adapter rod can also be pivotally fixed with respect to adjacent link 404 via cap 610. The adapter rod 604 and hook portions 605 may articulate to allow adjustable and lockable connections between rod 604 and rods 700. In an alternative embodiment, adapter rod 604 can be concave or bridge-shaped for easier connection to rods 700 by avoiding midline bony anatomy.

Figure 29:
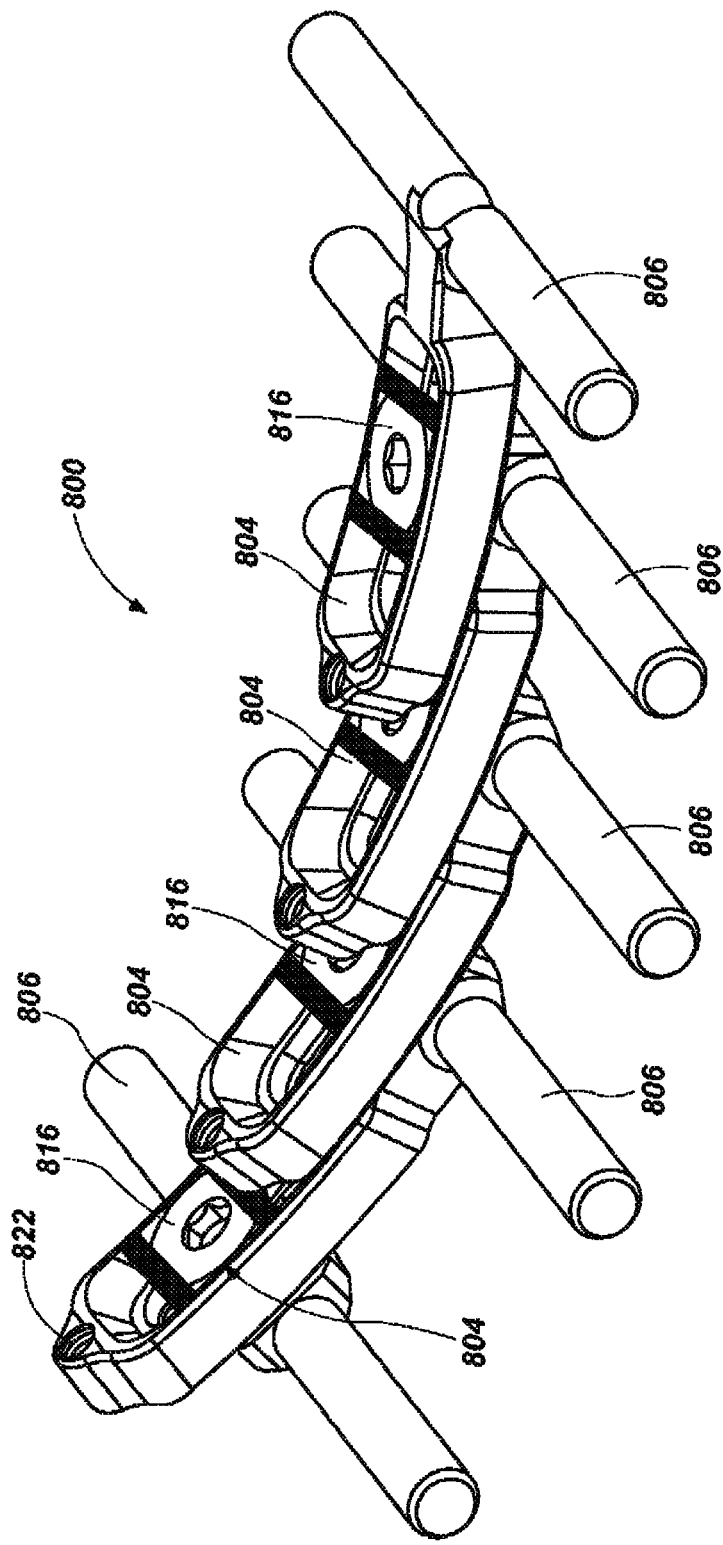
FIG. 29 is a perspective view of an embodiment of the present disclosure.

FIG. 29 illustrates a spinal stabilization apparatus 800 pursuant to an embodiment of the present disclosure. The apparatus 800 may include a plurality of transverse rods 806 attached to separate vertebrae by polyaxial tulip head screws similar to what is shown in FIG. 1. The apparatus 800 may comprise a plurality of longitudinal links 804 extending parallel to the spinal column and along a centerline of the spinal column, similar to FIGS. 6 and 7. The links 804 may overlap immediately adjacent links. Each link 804 may have similar features as links 104 disclosed above, including convex shape, elongated through-hole and interior through-hole geometry, and a bore 822 that may receive a spinous process anchor.

As opposed to the overlapping links 204 of FIGS. 6 and 7, links 804 are permanently fixed to adjacent links 804 via welding, glue or other desired fixing agent applied to bolts 816, for example. Alternatively, bolts 116 can include an internal aperture to allow insertion of internal screws (not shown), such that bolts 116 can expand radially as the screws are further inserted therein, which can further increase fixation within respective bores 214, 225, 314, 315, 443 or to respective links 104 and 404, for example. These internal screws may also be shaped to act as spinous process studs, similar to stud 460. Surface texturing of respective elements may also be used to further improve strength of fixation between such respective elements. Thus, unlike links of apparatuses 200 and 400, links 804 are not moveable with respect to one another.

Figure 30:
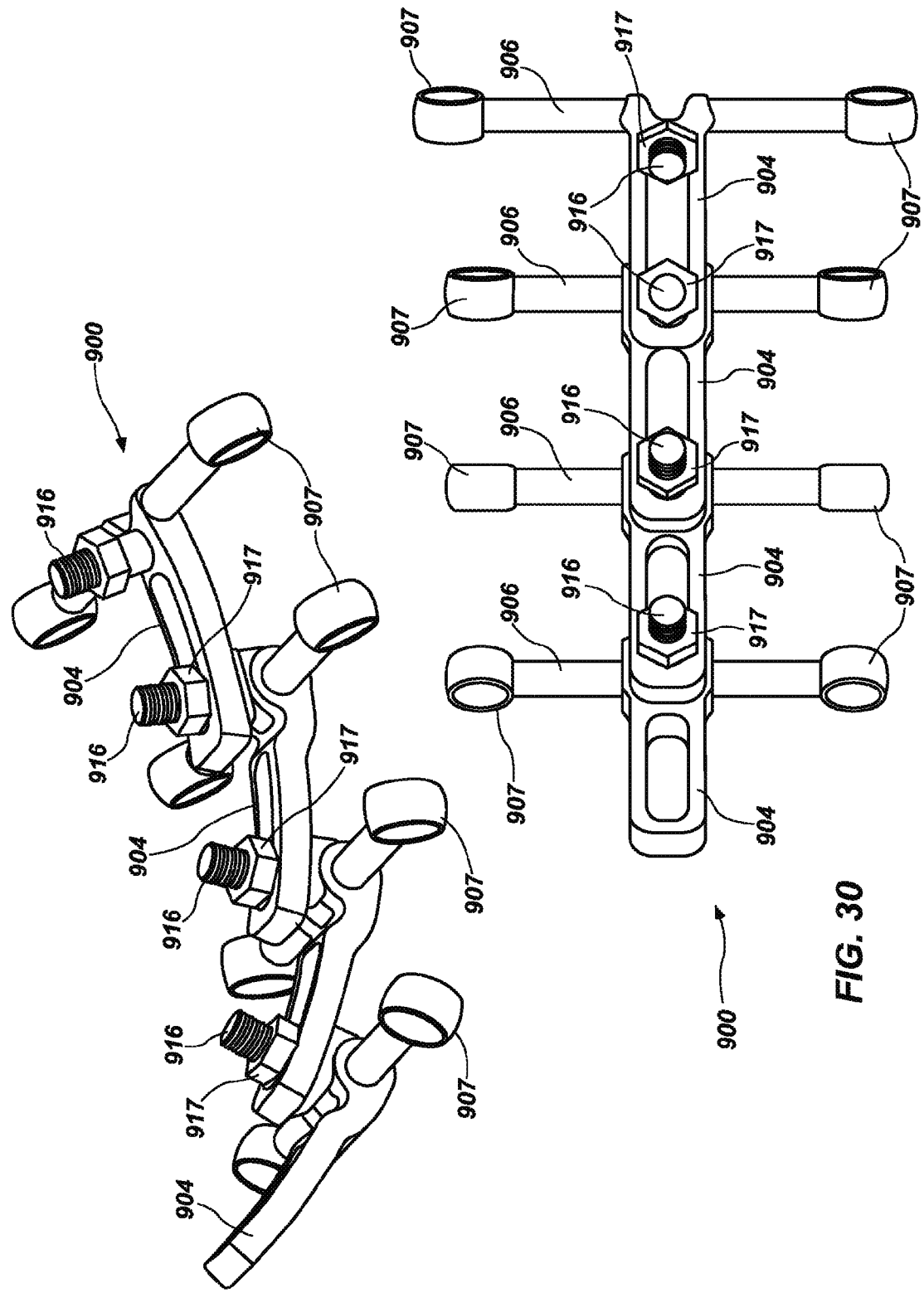
FIG. 30 is a perspective and top view of an embodiment of the present disclosure.

FIG. 30 illustrates a spinal stabilization apparatus 900 pursuant to an embodiment of the present disclosure. The apparatus 900 may include a plurality of transverse rods 906 attached to separate vertebrae by polyaxial tulip head screws similar to what is shown in FIG. 1. The apparatus 900 may comprise a plurality of longitudinal links 904 extending parallel to the spinal column and along a centerline of the spinal column, similar to FIGS. 6 and 7. The links 904 may overlap immediately adjacent links. Each link 904 may have similar features as links 104 disclosed above, including convex shape, elongated through-hole and interior through-hole geometry.

As opposed to the apparatus 200 having bolts 216 that extending down through the links 204 as shown in FIGS. 6 and 7, the apparatus 900 includes bolt shafts 916 that extend up through respective links 904 and engage respective nuts 917. As the nuts 917 engage with shafts 916 and tightened down onto links 904, adjacent links 904 become fixed with respect to one another.

Transverse rods 906 may also include hoops 907 at opposing terminating ends of the rods 906. The hoops 907 can act as anchor points for a distractor or compressor tool (not shown) which can extend through the hoops 907, enabling secured manipulation of the transverse rods 906. Additionally, the hoops 907 can be used as connecting features to engage connector rods (not shown) that extend substantially parallel to the spine, similar to connector rods 700 shown in FIG. 28. Connection rods substantially parallel to the spine may also be placed between adjacent hoops or multiple hoops and secured to hoops with grub screws or other fastening connectors. For example, grub screws or other desired fasteners can be used in conjunction with the hoops 907 to secure connector rods, from a single rod or dual rod system, to the apparatus 900.

FIG. 30A illustrates a spinal stabilization apparatus 950 pursuant to an embodiment of the present disclosure. The apparatus 950 may include a plurality of transverse rods 956 attached to separate vertebrae by polyaxial tulip head screws similar to what is shown in FIG. 1. The apparatus 950 may comprise a plurality of longitudinal links 954 extending parallel to the spinal column and along a centerline of the spinal column, similar to FIGS. 6 and 7. The links 954 may overlap immediately adjacent links. Each link 954 may have similar features as links 104 disclosed above, including convex shape, elongated through-hole and interior through-hole geometry.

Similar to the apparatus 200 having bolts 216, apparatus 950 also includes bolts 966 that extend down through the links 954 as shown in FIG. 30A.

Transverse rods 956 may also include hoops 957 at opposing terminating ends of the rods 956. The hoops 957 can act as anchor points for a distractor or compressor tool (not shown) which can extend through the hoops 957, enabling secured manipulation of the transverse rods 956. Additionally, the hoops 957 can be used as connecting features to engage connector rods (not shown) that extend substantially parallel to the spine, similar to connector rods 700 shown in FIG. 28. Connection rods substantially parallel to the spine may also be placed between adjacent hoops or multiple hoops and secured to hoops with grub screws or other fastening connectors. For example, grub screws or other desired fasteners can be used in conjunction with the hoops 957 to secure connector rods, from a single rod or dual rod system, to the apparatus 950.

Figure 31:
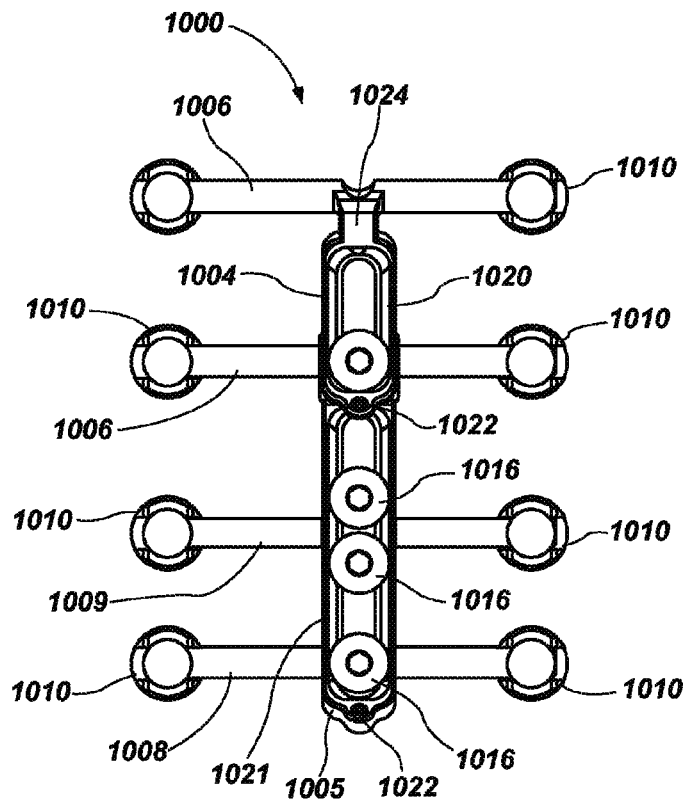
FIG. 31 is a top view of an embodiment of the present disclosure.
Figure 32:
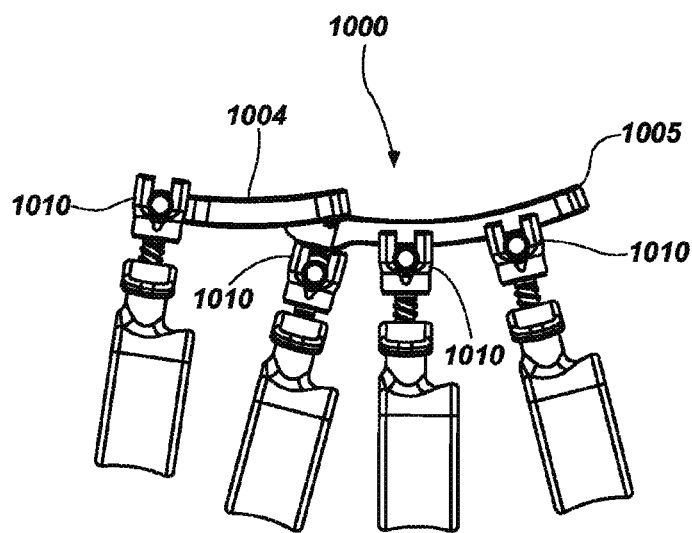
FIG. 32 is a side view of the embodiment of FIG. 31.

FIGS. 31 and 32 illustrate a spinal stabilization apparatus 1000 pursuant to an embodiment of the present disclosure. The apparatus 1000 may include a plurality of transverse rods 1006, 1008 and 1009. The transverse rods 1006, 1008, and 1009 may be attached to separate vertebrae by polyaxial tulip head screws 1010 similar to those shown in FIG. 1. The apparatus 1000 may comprise a central connector that includes a plurality of longitudinal links 1004 and 1005 extending substantially parallel to the spinal column and along a centerline of the spinal column. The links 1004 and 1005 may overlap similar to the embodiment illustrated in FIG. 6. Links 1004 and 1005 may have similar features as link 104 disclosed above, including convex shape, elongated through-holes 1020 and 1021 with similar interior through-hole geometry, and bores 1022 that may receive a spinous process anchor. Also similar to link 104, links 1004 and 1005 may be pivotally and translationally fixed to respective transverse rods 1006 via respective bridges 1024.

To assemble the apparatus 1000, transverse rods 1008 and 1009 may be secured to adjacent vertebra using respective head screws 1010. The head screws 1010 fix the respective transverse rods 1008 and 1009 with respect to the vertebra. Transverse rod 1006 corresponding to link 1005 can also be fixed to an adjacent vertebrae via head screws 1010. Due to the extended length of through-hole 1021 of link 1005, both transverse rods 1008 and 1009 can be secured to link 1005 via bolts 1016 extending through the through-hole.

As shown in FIG. 31, transverse rod 1009 can receive two bolts 1016, to better secure the orientation of transverse rod 1009 with respect to link 1005. Having two bolts 1016 secured to the same transverse rod 1009 can add strength to the connection between the transverse rod 1009 and the link 1005, providing a double foundation. Such a double foundation transverse rod connection be used at any vertebral level.

Another method of connecting link 1005 with transverse rod 1009 can include using a temporary long bolt to reduce deformity and a second standard bolt 1010 to secure the relative position. Then the temporary long bolt could be replaced with a more permanent standard length bolt 1010.

As shown in FIGS. 31 and 32, each adjacent 1004 is overlapped and fixed to the immediately adjacent link 1005 via a bolt 1016 which passes through the through-hole 1020 and is received by a bore in link 1005, as shown in FIGS. 31 and 32.

Figure 33A:
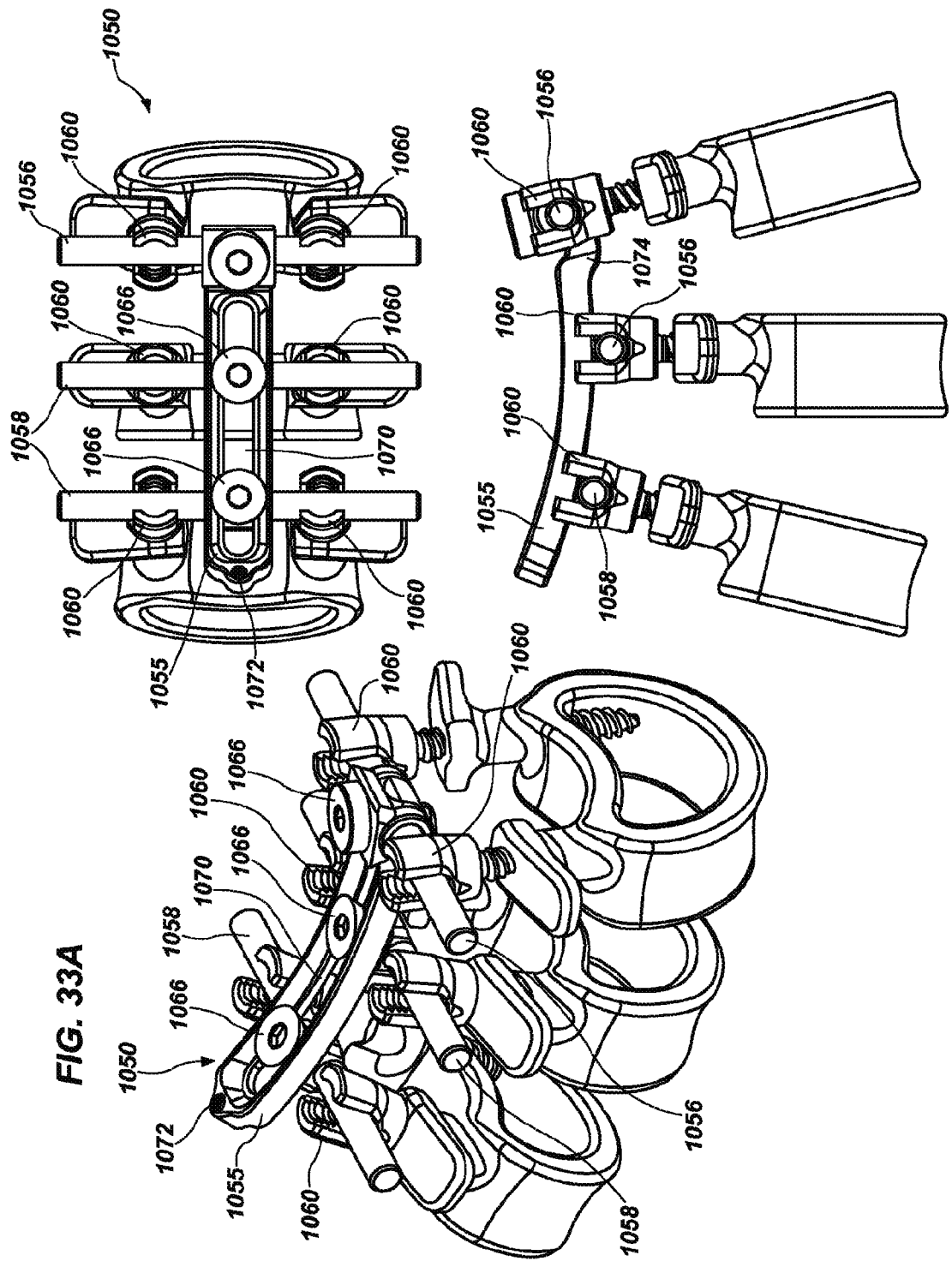
FIG. 33A is a perspective, side and top view of an embodiment of the present disclosure.
Figure 33B:
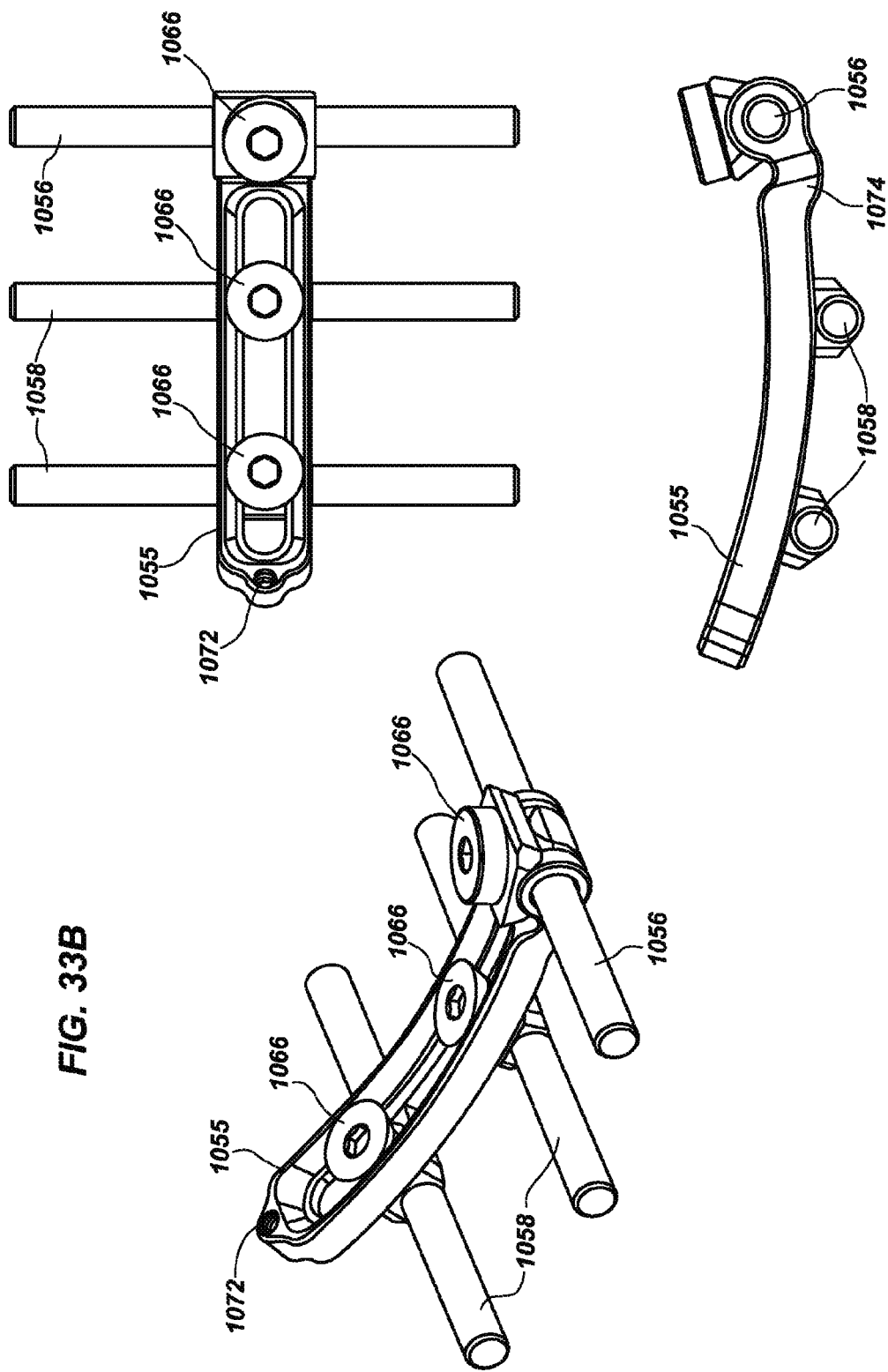
FIG. 33B is an isolated perspective, side and top view of the embodiment of FIG. 33A.

FIGS. 33A and 33B illustrate a spinal stabilization apparatus 1050 pursuant to an embodiment of the present disclosure. The apparatus 1050 may include a plurality of transverse rods 1056 and 1058. The transverse rods 1056, and 1058 may be attached to separate vertebrae by polyaxial tulip head screws 1060 similar to those shown in FIG. 1. The apparatus 1050 may comprise a central connector that includes a longitudinal link 1055 extending substantially parallel to the spinal column and along a centerline of the spinal column. Link 1055 may have similar features as link 104 disclosed above, including convex shape, elongated through-hole 1070 with a similar interior through-hole geometry, and a bore 1072 that may receive a spinous process anchor. Also similar to link 104, link 1055 may be pivotally and translationally fixed to respective transverse rod 1056 via bridges 1074.

To assemble the apparatus 1050, transverse rods 1058 may be secured to adjacent vertebra using respective head screws 1060. The head screws 1060 fix the respective transverse rods 1008 with respect to the vertebra. Due to the extended length of through-hole 1070 of link 1055, transverse rods 1058 can be secured to link 1055 via bolts 1066 extending through the through-hole 1070.

Another method of connecting link 1055 with transverse rod 1058 can include using a temporary long bolt to reduce deformity and a second standard bolt 1060 to secure the relative position. Then the temporary long bolt could be replaced with a more permanent standard length bolt 1060.

Figure 34:
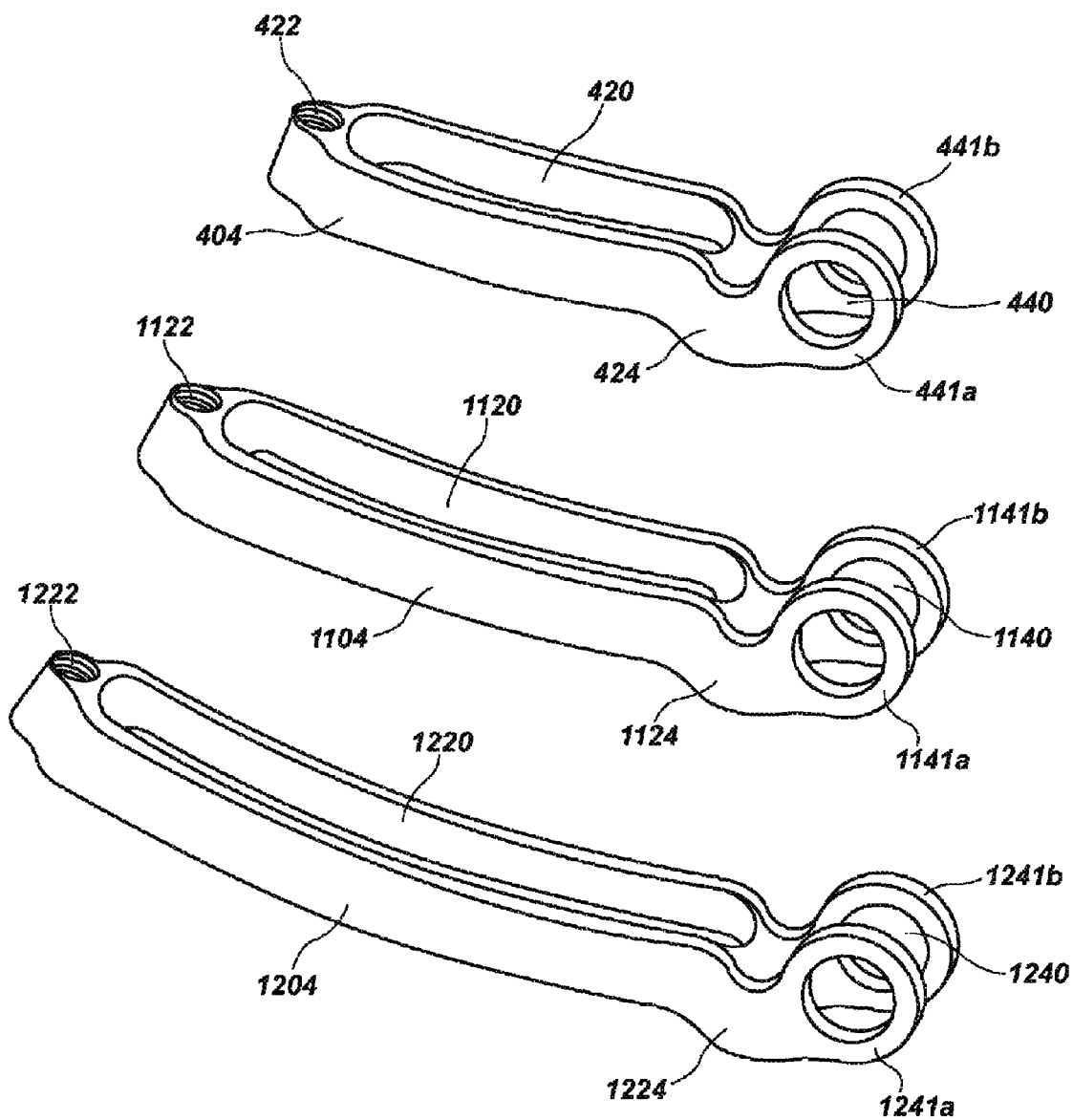
FIG. 34 is a perspective view of an embodiment of the present disclosure.

FIG. 34 illustrates isolated perspective views of links 404, 1104 and 1204. Although link 404 is discussed in detail above, link 404 is shown again in FIG. 34 to illustrate the comparative lengths of links 404, 1104 and 1204. Links 1104 and 1204 share many of the same, or substantially the same features, as link 404. For example, links 1104 and 1204 include elongated through-holes 1120 and 1220, however, links 1104 and 1204 have greater lengths and through-holes 1120 and 1220 have correspondingly greater lengths as well. Each link 1104 and 1204 may have other similar features as link 404 disclosed above, including convex shape, interior through-hole geometry, and a bore 1122 and 1222 that may receive a spinous process anchor.

The extended lengths of links 1104 and 1204 enable multiple transverse rods (similar to those shown in FIGS. 11 and 14) to be coupled though the same through-hole 1120 and 1220 enabling the use of a single link 1104 or 1204, for example, to connect with multiple levels of vertebra via transverse rods. This embodiment can create a less bulky system, while still enabling effective correction of the spine. Links 1104 and 1204 also include a bridge 1124 and 1224, similar to bridge 424, which can connect the link 1104 and 1204 to a corresponding transverse rod (not shown). A transverse rod can extend through channel 1140 and 1240 formed through hoops 1141a/1141b and 1241a/1241b, which can be integral with link corresponding links 1104 and 1204 via corresponding bridges 1124 and 1224. In alternative embodiments, links 1104 and 1204 can include static, rotationally fixed, transverse rods, similar to the link 104 and corresponding rod 106 shown in FIG. 3, which can enable the use of a singe link 1104 or 1204 to span and connect multiple levels of vertebra.

In accordance with the features and combinations described above, an apparatus for stabilizing a spine may comprise:

a plurality of transverse members, each of the transverse members attached to a vertebra by screws; and a longitudinal link, the longitudinal link secured to each of the transverse members.

In accordance with the features and combinations described above, a useful method of spinal fixation includes the steps of:

attaching a plurality of transverse rods to a respective plurality of vertebra, wherein each of the transverse rods are translationally fixed to a respective link;

connecting adjacent links, enabling longitudinal translation between connected links, while substantially preventing lateral translation between connected links;

manipulating at least one of the plurality of vertebra, to a desired position; and fixing adjacent links, substantially preventing any respective movement between adjacent links.

Those having ordinary skill in the relevant art will appreciate the advantages provide by the features of the present disclosure. For example, it is a feature of the present disclosure to provide an apparatus for spinal fixation. Another feature of the present disclosure to provide such an apparatus with a plurality of longitudinal links having a common longitudinal axis and a plurality of transverse members. It is a further feature of the present disclosure, in accordance with one aspect thereof, to provide an apparatus for spinal fixation that includes longitudinal links that are moveable with respect to immediately adjacent links.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An apparatus for stabilizing a spine, comprising:
a plurality of transverse rods, each of the transverse rods attachable to a vertebra;

a single central connector, comprising:
a plurality of links, each link having an elongated through-hole,
wherein each of the links are connected to, and in contact with, adjacent links through the elongated through-hole and each of the links are substantially aligned along a longitudinal axis;
wherein at least one connecting fastener extends through the elongated through-hole of at least one of the plurality of links, such that a longitudinal axis of the at least one connecting fastener intersects with one of the plurality of transverse rods; and
wherein each of the plurality of transverse rods are translationally fixed to at least one of the plurality of links, wherein at least one of the links is fixed to a bridge between the link and at least one of the transverse rods, the bridge having a smaller width than the link.

2. The apparatus of claim 1, wherein the through-hole of at least one of the plurality of links extends a distance more than half the length of the at least one link.

3. The apparatus of claim 1, wherein at least one of the transverse rods includes a concave portion for accommodating a spinous process.

4. The apparatus of claim 1, wherein the single central connector is coupled to a pair of longitudinal rods adapted to extend substantially parallel to the spine.

5. The apparatus of claim 1, wherein an inner surface of the elongated through-hole of each of the links includes a flange that extends substantially parallel and perpendicular with at least one of the transverse rods.

6. An apparatus for stabilizing a spine, comprising:
a plurality of transverse rods, each of the transverse rods attachable to a vertebra;
a single central connector, comprising:
a plurality of links,
wherein each of the links overlaps adjacent links, and each of the links are substantially aligned along a longitudinal axis; and
wherein each of the plurality of transverse rods are translationally fixed to at least one of the plurality of links; and
wherein at least one of the links is fixed to a bridge between the at least one link and at least one of the transverse rods, the bridge configured to receive the at least one transverse rod and at least one fastener.

7. The apparatus of claim 6, wherein at least one of the plurality of links includes an elongated through-hole.

8. The apparatus of claim 7, wherein the through-hole of the at least one of the plurality of links extends a distance more than half the length of the at least one link.

9. The apparatus of claim 7, wherein an inner surface of the through-hole includes a flange that extends parallel with at least one of the transverse rods.

10. The apparatus of claim 7, wherein at least one connecting fastener extends through the elongated through-hole of at least one of the plurality of links, such that a longitudinal axis of the connecting fastener intersects with one of the plurality of transverse rods.

11. The apparatus of claim 6, wherein at least one of the transverse rods includes a concave portion for accommodating a spinous process.

12. The apparatus of claim 6, wherein the bridge having a smaller width than the link.

13. The apparatus of claim 6, wherein the single central connector is coupled to a pair of longitudinal rods adapted to extend substantially parallel to the spine.

14. The apparatus of claim 6, wherein at least one of the plurality transverse rods resides entirely between imaginary extension surfaces extending from upper and lower surfaces of at least one of the plurality of links and along a same path, route or direction of said upper and lower surfaces of said at least one of the plurality of links.

15. An apparatus for stabilizing a spine, comprising:
a plurality of transverse rods, each of the transverse members attachable to a vertebra;
a single central connector, comprising:
a plurality of links,
wherein each of the links are connected to, and abut, adjacent links such that each of the links are movable with respect to adjacent links while connected;
wherein each of the plurality of transverse rods are translationally fixed to at least one of the plurality of links; and
wherein at least one of the links is fixed to a bridge between the at least one link and at least one of the transverse rods, the bridge configured to receive the at least one transverse rod and at least one fastener.

16. The apparatus of claim 15, wherein at least one of the plurality of links includes an elongated through-hole.

17. The apparatus of claim 16, wherein the through-hole of the at least one of the plurality of links extends a distance more than half the length of the at least one link.

18. The apparatus of claim 16, wherein at least one connecting fastener extends through the elongated through-hole of at least one of the plurality of links, such that a longitudinal axis of the connecting fastener intersects with one of the plurality of transverse rods.

19. The apparatus of claim 15, wherein at least one of the transverse rods includes a concave portion for accommodating a spinous process.

20. The apparatus of claim 15, wherein the bridge having a smaller width than the link.

21. The apparatus of claim 15, wherein the single central connector is coupled to a pair of longitudinal rods adapted to extend substantially parallel to the spine.

22. The apparatus of claim 15, wherein an inner surface of the through-hole includes a flange that extends parallel with at least one of the transverse rods.

23. An apparatus for stabilizing a spine, comprising:
a plurality of transverse rods, each of the transverse rods attachable to a vertebra;
a plurality of tulip screws configured to attach each of the plurality of transverse rods to a vertebra;
a central connector, comprising:
a plurality of links, each link having a substantially convex shape and an elongated through-hole, an inner surface of each of the through-holes including a flange that extends parallel and perpendicular with at least one of the transverse rods,
wherein each of the links are connected to adjacent links via at least one bolt that extends through the elongated through-hole, and each of the links are substantially aligned along a longitudinal axis;
at least one of the links being fixed to a bridge between the link and at least one of the transverse rods, the bridge having a smaller width than the link and the bridge have a substantially concave shape; and wherein each of the plurality of transverse rods are translationally fixed to at least one of the plurality of links, and at least one of the transverse rods includes a concave portion for accommodating a spinous process;
a pair of longitudinal rods adapted to extend substantially parallel to the spine, the pair of longitudinal rods coupled to the central connector;
a threaded bore extending into the link; and
a spinous process anchor having a threaded end and an eyelet, wherein the threaded end is configured to threadedly engage the bore and the eyelet is configured facilitate suturing tissue.

24. An apparatus for stabilizing a spine, comprising:
a plurality of transverse rods, each of the transverse rods attachable to a vertebra;
a single central connector, comprising:
    a plurality of links, each link having an elongated through-hole,
        wherein each of the links are connected to adjacent links through the elongated through-hole and each of the links are substantially aligned along a longitudinal axis;
    wherein each of the plurality of transverse rods are translationally fixed to at least one of the plurality of links;
    wherein at least one connecting fastener extends through the elongated through-hole of at least one of the plurality of links, such that a longitudinal axis of the at least one connecting fastener intersects with one of the plurality of transverse rods; and
    wherein the single central connector is coupled to a pair of longitudinal rods adapted to extend substantially parallel to the spine, wherein at least one of the links is fixed to a bridge between the link and at least one of the transverse rods, the bridge configured to receive the transverse rod and at least one fastener.

25. An apparatus for stabilizing a spine, comprising:
a plurality of transverse rods, each of the transverse rods attachable to a vertebra;
a single central connector, comprising:
    a plurality of links, each link having an elongated through-hole,
        wherein each of the links are connected to adjacent links through the elongated through-hole and each of the links are substantially aligned along a longitudinal axis;
    wherein each of the plurality of transverse rods are translationally fixed to at least one of the plurality of links;
    wherein at least one connecting fastener extends through the elongated through-hole of at least one of the plurality of links, such that a longitudinal axis of the at least one connecting fastener intersects with one of the plurality of transverse rods; and
    wherein an inner surface of the through-hole includes a flange that extends substantially parallel and perpendicular with at least one of the transverse rods, wherein at least one of the links is fixed to a bridge between the link and at least one of the transverse rods, the bridge configured to receive the transverse rod and at least one fastener.

26. An apparatus for stabilizing a spine, comprising:
a plurality of transverse rods, each of the transverse rods attachable to a vertebra,
a single central connector, comprising:
    a plurality of links, wherein each of the links overlaps adjacent links, and each of the links are substantially aligned along a longitudinal axis;
    wherein each of the plurality of transverse rods are connected to at least one of the plurality of links,
    wherein at least one of the links is fixed to a bridge between the at least one link and at least one of the transverse rods, the bridge configured to receive the at least one transverse rod and at least one fastener, and
    wherein at least one of the plurality of links includes an elongated through-hole and at least one connecting fastener extends through the elongated through-hole of at least one of the plurality of links, such that a longitudinal axis of the connecting fastener intersects with one of the plurality of transverse rods.

27. The apparatus of claim 26, wherein the through-hole of the at least one of the plurality of links extends a distance more than half the length of the at least one link.

28. The apparatus of claim 26, wherein at least one of the transverse rods includes a concave portion for accommodating a spinous process.

29. The apparatus of claim 26, wherein the bridge having a smaller width than the link.

30. The apparatus of claim 26, wherein the single central connector is coupled to a pair of longitudinal rods adapted to extend substantially parallel to the spine.

31. The apparatus of claim 26, wherein an inner surface of the through-hole includes a flange that extends parallel with at least one of the transverse rods.

32. An apparatus for stabilizing a spine, comprising:
a plurality of transverse rods, each of the transverse rods attachable to a vertebra;
a single central connector, comprising:
    a plurality of links, each link having an elongated through-hole,
        wherein each of the links are connected to, and in contact with, adjacent links through the elongated through-hole and each of the links are substantially aligned along a longitudinal axis;
    wherein at least one connecting fastener extends through the elongated through-hole of at least one of the plurality of links, such that a longitudinal axis of the connecting fastener intersects with one of the plurality of transverse rods; and
    wherein each of the plurality of transverse rods are translationally fixed to at least one of the plurality of links, wherein at least one of the links is fixed to a bridge between the link and at least one of the transverse rods, the bridge configured to receive the transverse rod and at least one fastener.

\* \* \* \* \*